United States Patent
Liu et al.

(10) Patent No.: US 10,889,824 B2
(45) Date of Patent: Jan. 12, 2021

(54) METHOD FOR GENETIC TRANSFORMATION OF EDIBLE MUSHROOMS

(71) Applicant: Shanghai Academy of Agricultural Sciences, Shanghai (CN)

(72) Inventors: Jianyu Liu, Shanghai (CN); Xiaodong Shang, Shanghai (CN); Chunyan Song, Shanghai (CN); Qi Tan, Shanghai (CN); Zhen Xu, Shanghai (CN); Qiaozhen Li, Shanghai (CN); Dan Zhang, Shanghai (CN); Ruijuan Wang, Shanghai (CN); Hailong Yu, Shanghai (CN); Lujun Zhang, Shanghai (CN); Meiyan Zhang, Shanghai (CN); Hui Yang, Shanghai (CN); Yu Li, Shanghai (CN); Feng Zhou, Shanghai (CN); Ning Jiang, Shanghai (CN)

(73) Assignee: Shanghai Academy of Agricultural Sciences

(*) Notice: Subject to any disclaimer, the term of this patent is extended or adjusted under 35 U.S.C. 154(b) by 197 days.

(21) Appl. No.: 16/037,089

(22) Filed: Jul. 17, 2018

(65) Prior Publication Data
US 2019/0119668 A1 Apr. 25, 2019

(30) Foreign Application Priority Data
Oct. 23, 2017 (CN) .......................... 2017 1 0997662

(51) Int. Cl.
| | | |
|---|---|---|
| *C12N 15/80* | (2006.01) | |
| *C12N 13/00* | (2006.01) | |
| *C12N 15/87* | (2006.01) | |
| *C12N 1/14* | (2006.01) | |

(52) U.S. Cl.
CPC .............. *C12N 15/80* (2013.01); *C12N 1/14* (2013.01); *C12N 13/00* (2013.01); *C12N 15/87* (2013.01)

(58) Field of Classification Search
CPC ...................................................... C12N 15/80
See application file for complete search history.

(56) References Cited

U.S. PATENT DOCUMENTS

| | | | | |
|---|---|---|---|---|
| 4,063,383 A | * | 12/1977 | Green ................... | A01G 18/64 47/1.1 |
| 2002/0016982 A1 | * | 2/2002 | Romaine .............. | C12N 15/80 800/294 |

* cited by examiner

*Primary Examiner* — David H Kruse
(74) *Attorney, Agent, or Firm* — Harness, Dickey & Pierce, P.L.C.

(57) ABSTRACT

A method for genetic transformation of edible mushrooms is provided relating to the technical field of genetic transformation of *Agaricus bisporus*, enoki mushroom and shiitake. The disclosed method for genetic transformation of *Agaricus bisporus* includes: inoculating *Agaricus bisporus* liquid mycelia into a foxtail-millet-grain culture medium, and pre-culturing them at 20-25° C. until *Agaricus bisporus* mycelia grow on surfaces of foxtail millet grains. This method uses the foxtail millet grains as an attachment matrix, and during the pre-culturing and co-culturing, the culture substrate is shaken up every day. The method for genetic transformation of enoki mushroom or shiitake includes: inoculation of enoki mushroom mycelia or shiitake mycelia, activated culturing of *agrobacterium*, and *agrobacterium* infecting a foxtail millet grain-enoki mushroom mycelium matrix or a foxtail millet grain-shiitake mycelium matrix.

17 Claims, 3 Drawing Sheets
Specification includes a Sequence Listing.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Hyg-F primer

<400> SEQUENCE: 1
gatgttggcg acctcgtatt                20

<210> SEQ ID NO 2
<211> LENGTH: 22
<212> TYPE: DNA
<213> ORGANISM: Artificial Sequence
<220> FEATURE:
<223> OTHER INFORMATION: HYg-R primer

<400> SEQUENCE: 2
tcgttatgtt tatcggcact tt                22

METHOD FOR GENETIC TRANSFORMATION OF EDIBLE MUSHROOMS

CROSS-REFERENCE TO RELATED APPLICATION

This application claims priority to Chinese Patent Application No. 201710997662.4, filed on Oct. 23, 2017 with the State Intellectual Property Office (SIPO) of the People's Republic of China and entitled "Method for Genetic Transformation of *Agaricus Bisporus*", the contents of which are incorporated herein by reference in their entirety.

BACKGROUND

Technical Field

The present disclosure relates to the technical field of genetic transformation of edible mushrooms, and particularly, to a method for genetic transformation of *Agaricus bisporus*, enoki mushroom and shiitake (*Lentinus edodes*).

Background Art

The technology of genetic transformation is one of the important methods for carrying out edible mushroom molecule breeding and genetic function researches. However, the research of edible mushroom genetic engineering was started relatively late, and lack of a stable and efficient exogenous gene transformation system is a main obstacle restricting the development of performing genetic modification on edible mushrooms with a method of molecular biology.

SUMMARY

Embodiments of the present disclosure provide a method for genetic transformation of *Agaricus bisporus*, which is convenient in operation, high in transformation efficiency, easy in transformant separation, and has a good application prospect.

Embodiments of the present disclosure further provides a method for genetic transformation of edible mushrooms, which is convenient in operation, high in transformation efficiency, easy in transformant separation, and has a good application prospect.

Embodiments of the present disclosure further provides a method for genetic transformation of shiitake, which is convenient in operation, high in transformation efficiency, easy in transformant separation, and has a good application prospect.

Embodiments of the present disclosure can be achieved by following technical solutions:

A first aspect of the present disclosure provides a method for genetic transformation of *Agaricus bisporus*, which can include:

Step (a): inoculating liquid mycelia of *Agaricus bisporus* into a foxtail-millet-grain culture medium, and placing them in a condition of 20-25° C. for pre-culturing until *Agaricus bisporus* mycelia grow on surfaces of the foxtail millet grains, wherein the foxtail-millet-grain culture medium is shaken up every day during the pre-culturing;

Step (b): mixing the foxtail millet grains having the *Agaricus bisporus* mycelia with an induction culture medium, performing ultrasonic treatment and soaking treatment, discarding a supernatant, and collecting precipitated foxtail millet grains;

Step (c): mixing the foxtail millet grains obtained in Step (b) with an *agrobacterium* infection liquid containing target genes, performing ultrasonic treatment and static infection, performing absorption to remove the redundant *agrobacterium* bacterial liquid, and performing co-culturing in a condition of 20-25° C., wherein the foxtail millet grains are shaken up every day during the co-culturing; and Step (d): picking, after the co-culturing has ended, individual foxtail millet grains and transferring them to a screening culture medium, and performing screening culturing in a condition of 20-25° C.

Further, in some embodiments of the present disclosure, 100 ml of the induction culture medium can for example contain: K-buffer 0.8-1.2 ml, M-N solution 1.8-2.2 ml, 1% $CaCl_2$ 0.08-0.12 ml, 0.01% $FeSO_4$ 0.8-1.2 ml, 20% $NH_4NO_3$ 0.23-0.27 ml, Spore elements 0.48-0.52 ml, 50% glycerol 0.8-1.2 ml, 1 mol/L pH5.3 MES (2-(4-Morpholino)ethanesulfonic acid) 3.8-4.2 ml and 2 mol/L dextrose 0.48-0.52 ml.

Preferably, in some embodiments of the present disclosure, 100 ml of the induction culture medium can for example contain: K-buffer 1 ml, M-N solution 2 ml, 1% $CaCl_2$ 0.01 ml, 0.01% $FeSO_4$ 1 ml, 20% $NH_4NO_3$ 0.25 ml, Spore elements 0.5 ml, 50% glycerol 1 ml, 1 mol/L pH5.3 MES 4 ml and 2 mol/L dextrose 0.5 ml.

Further, in some embodiments of the present disclosure, 100 ml of the K-buffer can contain: $K_2HPO_4$ 18-22 g and $KH_2PO_4$ 14-15 g. A pH value of the K-buffer is 6.8-7.2.

Preferably, in some embodiments of the present disclosure, 100 ml of the K-buffer can contain: $K_2HPO_4$ 20 g and $KH_2PO_4$ 14.5 g. A pH value of K-buffer is 7.0.

Further, in some embodiments of the present disclosure, 100 ml of the M-N solution can contain: $MgSO_4.7H_2O$ 2.8-3.2 g and NaCl 1.3-1.7 g.

Preferably, in some embodiments of the present disclosure, 100 ml of the M-N solution can contain: $MgSO_4.7H_2O$ 3 g and NaCl 1.5 g.

Further, in some embodiments of the present disclosure, the Spore elements can be obtained by mixing 450-500 mg/L $ZnSO_4.7H_2O$, 450-500 mg/L $CuSO_4.5H_2O$, 450-500 mg/L $H_3BO_3$, 450-500 mg/L $MnSO_4.H_2O$ and 450-500 mg/L $NaMoO_4.2H_2O$ with equal volume proportions.

Preferably, in some embodiments of the present disclosure, the Spore elements can be obtained by mixing 500 mg/L $ZnSO_4.7H_2O$, 500 mg/L $CuSO_4.5H_2O$, 500 mg/L $H_3BO_3$, 500 mg/L $MnSO_4.H_2O$ and 500 mg/L $NaMoO_4.2H_2O$ with equal volume proportions.

Furthermore, in some embodiments of the present disclosure, a mass volume ratio (g:ml) of the foxtail millet grains to the induction culture medium can be 1:1.3-1.7. An amount of the *agrobacterium* infection liquid used in Step (c) is preferably consistent with an amount of the induction culture medium used in Step (b).

Preferably, in some embodiments of the present disclosure, the mass volume ratio (g:ml) of the foxtail millet grains to the induction culture medium can be 1:1.5 in Step (b).

Further, in some embodiments of the present disclosure, in Step (b), the ultrasonic treatment can be carried out under a frequency of 40-60 KHz and a power of 140-160 W for 1 min-2 min, and the soaking treatment can last for 10-15 min.

Furthermore, in some embodiments of the present disclosure, in Step (b), the ultrasonic treatment can be carried out under a frequency of 40-60 KHz and a power of 140-160 W for 10 s-30 s. The static infection can last for 20-30 min.

Furthermore, in some embodiments of the present disclosure, 1 L of the screening culture medium can for example contain: potato 190-210 g, dextrose 18-22 g and agar powder 18-22 g.

It should be indicated that:

The foxtail-millet-grain culture medium in Step (a) can be prepared through the methods as follows, but not limited to the following: cleaning the foxtail millet grains, soaking the foxtail millet grains with distilled water for 18-30 min to makel the foxtail millet grains become slightly soft, dispersing the foxtail millet grains on a gauze for absorbing moisture, then placing the foxtail millet grains into a triangular flask, and carrying out high-temperature high-pressure sterilization to obtain the foxtail-millet-grain culture medium.

The liquid mycelia of *Agaricus bisporus* in Step (a) can be prepared through a method as follows, but not limited to the following: transferring the *Agaricus bisporus* mycelia cultured on a solid culture medium, together with the culture medium, into a homogenizer, adding a liquid culture medium, and intermittently smashing them to obtain the liquid mycelia of *Agaricus bisporus*.

The *agrobacterium* infection liquid in Step (c) can be prepared through a method as follows, but not limited to the following: carrying out streak inoculation for *agrobacterium* containing a binary expression vector on a solid culture medium containing corresponding antibiotics, culturing the *agrobacterium* at 28° C. for 2-3 days; then picking single colonies to inoculate them in the liquid culture medium for culturing at 28° C. and 180-220 r/min until $OD_{600}$=0.5-0.6; and then re-suspending the *agrobacterium* bacterial liquid in the induction culture medium for culturing at 28° C. and 180-220 r/min until $OD_{600}$=0.5-0.6, to obtain the *agrobacterium* infection liquid that can be used for infection.

A second aspect of the present disclosure provides a method for genetic transformation of enoki mushroom, which can include: (1) transferring, into a homogenizer, enoki mushroom mycelia cultured on a solid culture medium together with the culture medium, adding a liquid culture medium, and intermittently smashing them to obtain liquid mycelia; and inoculating the liquid mycelia into a foxtail-millet-grain culture medium for culturing at 20-25° C. for 8-10 days, wherein shaking is performed every day during the culturing until the foxtail millet grains become white;

(2) carrying out streak inoculation for *agrobacterium* containing a binary expression vector on a solid culture medium containing corresponding antibiotics, culturing the *agrobacterium* at 28° C. for 2-3 days; then picking single colonies to inoculate them in the liquid culture medium for culturing at 28° C. and 180-220 r/min until $OD_{600}$=0.5-0.6; and then re-suspending an *agrobacterium* bacterial liquid in an induction culture medium for culturing at 28° C. and 180-220 r/min until $OD_{600}$=0.5-0.6;

(3) adding the foxtail millet grains of Step (1) to a container, adding the induction culture medium, performing ultrasonic treatment and soaking treatment, and removing a supernatant by absorption, wherein the ultrasonic treatment can be carried out under a frequency of 40-60 KHz and a power of 140-160 W for 1 min-2 min, and the soaking treatment can last for 10-15 min; and (4) adding the *agrobacterium* bacterial liquid of Step (2) to Step (3), performing ultrasonic treatment and static infection, absorbing redundant bacterial liquid for removal, and performing culturing in a condition of 20-25° C. for no less than 72 hours, wherein shaking is performed every day during the culturing; finally, picking individual foxtail millet grains and transferring them to induction culture medium plates for culturing at 20-25° C. for 7-10 days, wherein the ultrasonic treatment can be carried out under a frequency of 40-60 KHz and a power of 140-160 W for 10 s-20 s, and the static infection can last for 20-30 min.

A third aspect of the present disclosure provides a method for genetic transformation of shiitake, which can include: (1) transferring shiitake mycelia cultured on a solid culture medium, together with the culture medium, into a homogenizer, adding a liquid culture medium, and intermittently smashing them to obtain liquid mycelia; then inoculating the liquid mycelia into a foxtail-millet-grain culture medium for culturing at 20-25° C. for 15-20 days, wherein shaking is performed every day during the culturing until foxtail millet grains became white;

(2) carrying out streak inoculation for *agrobacterium* containing a binary expression vector on a solid culture medium containing corresponding antibiotics, and culturing the *agrobacterium* at 28° C. for 2-3 days; then picking single colonies to inoculate them in the liquid culture medium for culturing at 28° C. and 180-220 r/min until $OD_{600}$=0.5-0.6; and then re-suspending the *agrobacterium* bacterial liquid in an induction culture medium for culturing at 28° C. and 180-220 r/min until $OD_{600}$=0.5-0.6;

(3) adding the foxtail millet grains of Step (1) to a container, adding the induction culture medium, performing ultrasonic treatment and soaking treatment, removing a supernatant by absorption, wherein the ultrasonic treatment can be carried out under a frequency of 40-60 KHz and a power of 140-160 W for 1 min-2 min, and the soaking treatment can last for 10-15 min; and (4) adding the *agrobacterium* bacterial liquid of Step (2) to Step (3), performing ultrasonic treatment and static infection, absorbing redundant bacterial liquid for removal, and performing culturing in a condition of 20-25° C. for 72 hours or longer, wherein shaking is performed every day during the culturing; finally, picking individual foxtail millet grains and transferring them to induction culture medium plates for culturing at 20-25° C. for 7-10 days, wherein the ultrasonic treatment can be carried out under a frequency of 40-60 KHz and a power of 140-160 W for 10 s-20 s, and the static infection can last for 20-30 min.

In some embodiments of the present disclosure, in genetic transformation methods of enoki mushroom or shiitake, a method for preparing the foxtail-millet-grain culture medium in Step (1) for example can include, for example: cleaning the foxtail millet grains, soaking the foxtail millet grains with distilled water for 18-30 min to makel the foxtail millet grains become slightly soft, dispersing the foxtail millet grains on a gauze for absorbing moisture, then placing the foxtail millet grains into a triangular flask, and carrying out high-temperature high-pressure sterilization.

In some embodiments of the present disclosure, in the genetic transformation methods of enoki mushroom or shiitake, a formula of the induction culture medium in Step (2) and Step (3) for example can contain: K-buffer 1 ml, M-N solution 2 ml, 1% $CaCl_2$ 0.1 ml, 0.01% $FeSO_4$ 1 ml, 20% $NH_4NO_3$ 0.25 ml, Spore elements 0.5 ml, 50% glycerol 1 ml, 1 mol/L pH5.3 MES 4 ml and 2 mol/L dextrose 0.5 ml, wherein in preparation, they are diluted with sterile dd$H_2O$ to 100 ml.

In some embodiments of the present disclosure, in the genetic transformation methods of enoki mushrooms or shiitake, the K-buffer for example can contain: $K_2HPO_4$ 20 g and $KH_2PO_4$ 14.5 g, a pH value of which is adjusted to 7.0 with KOH, and which are diluted with sterile dd$H_2O$ to 100 ml.

In some embodiments of the present disclosure, in the genetic transformation methods of enoki mushrooms or shiitake, the M-N solution for example can contain: $MgSO_4 \cdot 7H_2O$ 3 g and NaCl 1.5 g, wherein in preparation, they are diluted with sterile $ddH_2O$ to 100 ml.

In some embodiments of the present disclosure, in the genetic transformation methods of enoki mushrooms or shiitake, the Spore elements can be obtained by mixing 450-550 mg/L $ZnSO_4 \cdot 7H_2O$, 450-550 mg/L $CuSO_4 \cdot 5H_2O$, 450-550 mg/L $H_3BO_3$, 450-550 mg/L $MnSO_4 \cdot H_2O$ and 450-550 mg/L $NaMoO_4 \cdot 2H_2O$ with equal volume proportions, filtering and sterilizing, and is stored 4° C.

Preferably, the above Spore elements for example can contain: 500 mg/L $ZnSO_4 \cdot 7H_2O$, 500 mg/L $CuSO_4 \cdot 5H_2O$, 500 mg/L $H_3BO_3$, 500 mg/L $MnSO_4 \cdot H_2O$ and 500 mg/L $NaMoO_4 \cdot 2H_2O$.

In some embodiments of the present disclosure, in the genetic transformation methods of enoki mushroom or shiitake, a ratio of the foxtail millet grains to the induction culture medium to the *agrobacterium* bacterial liquid added in Step (3) for example can be 1 g:(1.3-1.7) ml:(1.3-1.7) ml.

Preferably, the ratio of the foxtail millet grains to the induction culture medium to the *agrobacterium* bacterial liquid added in Step (3) for example can be 1 g:1.5 ml:1.5 ml.

The present disclosure has the following beneficial effects:

The method for genetic transformation of edible mushrooms provided in the present disclosure uses the foxtail millet grains as attachment matrix for growth of the *Agaricus bisporus* mycelia or the enoki mushroom mycelia or the shiitake mycelia, and during the pre-culturing and co-culturing, the culture medium is shaken up every day, so that the mycelia grow evenly on the foxtail millet grains, moreover, with impact force generated during shaking, wounds can be randomly created on the mycelia attached to the foxtail millet grains, which is more advantageous to the *agrobacterium* infection reaction, and improves the transformation rate.

Through the ultrasonic treatment, it can significantly promote the *agrobacterium* to infect the mycelia and improve the transformation rate; moreover, each foxtail millet grain can be used as a separate transformation individual, then the operation and statistics are more quick and convenient, and the separation is also easier.

Compared with the existing genetic transformation methods, the method for genetic transformation of edible mushrooms provided in the present disclosure is convenient in operation, high in transformation efficiency, easy in transformant separation, and has a good application prospect.

BRIEF DESCRIPTION OF THE DRAWINGS

In order to more clearly illustrate technical solutions of examples of the present disclosure, figures which are needed for description of the examples will be introduced below briefly. It should be understood that the figures below merely show some examples of the present disclosure, and therefore should not be considered as limiting the scope. A person ordinarily skilled in the art still can obtain other relevant figures according to these figures, without doing creative work.

DETAILED DESCRIPTION OF EMBODIMENTS

Figure 1:
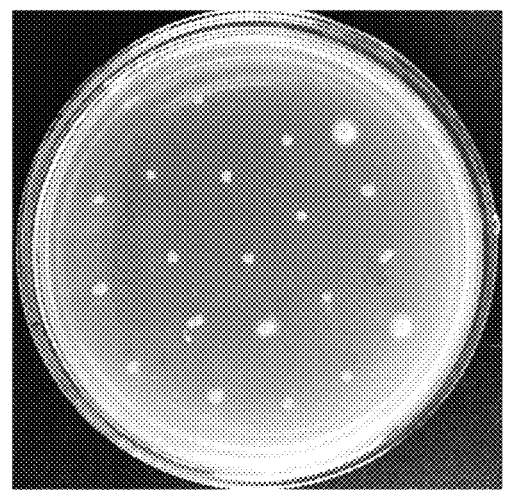
FIG. 1 shows a growth state of transformants on a re-screening culture medium in Example 1 of the present disclosure.

In order to make the objects, technical solutions and advantages of the examples of the present disclosure clearer, the technical solutions in the examples of the present disclosure will be described below clearly and completely. If no specific conditions are specified in the examples, they are carried out under normal conditions or conditions recommended by the manufacturer. If the manufacturers of reagents or apparatus used are not specified, they are conventional products commercially available. Methods for genetic transformation of edible mushrooms in examples of the present disclosure are specifically described below.

The methods for genetic transformation of edible mushrooms provided in examples of the present disclosure mainly involves but not limited to *Agaricus bisporus*, enoki mushroom and shiitake among edible mushrooms.

In the above, a method for genetic transformation of *Agaricus bisporus* can include:

Step (a): inoculating *Agaricus bisporus* liquid mycelia into a foxtail-millet-grain culture medium, and placing them in a condition of 20-25° C. for pre-culturing until *Agaricus bisporus* mycelia grow on surfaces of the foxtail millet grains, to obtain a complex of foxtail millet grain and *Agaricus bisporus* mycelium, wherein the foxtail-millet-grain culture medium is shaken up (or shaken) every day during the pre-culturing.

Optionally, the above *Agaricus bisporus* liquid mycelia for example can be obtained in a manner as follows, but not limited to the following: transferring *Agaricus bisporus* mycelia cultured on a solid culture medium, together with the culture medium, into a homogenizer, adding a liquid culture medium, and intermittently smashing them.

The above solid culture medium can be a potato-dextrose-agar (PDA) culture medium, the *Agaricus bisporus* mycelia can be *Agaricus bisporus* monokaryon s73 mycelia, and the culture medium transferred to the homogenizer can have a size of (45-55) mm×(45-55) mm, preferably 50 mm×50 mm.

Optionally, preferably, *Agaricus bisporus* monokaryon s73 mycelia cultured on the potato-dextrose-agar culture medium for 18-22 days are picked, and more preferably, *Agaricus bisporus* monokaryon s73 mycelia cultured on the potato-dextrose-agar culture medium for 20 days are picked.

Optionally, the above solid culture medium can be a potato-dextrose-broth (PDB) culture medium, and an amount of added potato-dextrose-broth (PDB) culture medium, for example, can be 80-120 ml, preferably 100 ml.

Optionally, the intermittent smashing for example can last for 25-35 s, preferably 30 s.

Optionally, the foxtail-millet-grain culture medium in the above Step (a) can be prepared with reference to a following method, but not limited to the following: cleaning the foxtail millet grains, soaking the foxtail millet grains with distilled water for 18-30 min to make the foxtail millet grains become slightly soft, dispersing the foxtail millet grains on a clean gauze for absorbing moisture, then placing the foxtail millet grains into a triangular flask, and carrying out high-temperature high-pressure sterilization.

The above soaking can last for 18-22 min, for example 18 min, 20 min and 22 min.

Optionally, 30 g of the foxtail millet grains can be placed in a triangular flask of 250 ml to undergo sterilization. The sterilization can be carried out in a condition of 120° C. for 28-32 min, for example, 28 min, 30 min and 32 min.

Step (b): mixing the above foxtail millet grains having the *Agaricus bisporus* mycelia with an induction culture medium, performing ultrasonic treatment and soaking treatment, discarding a supernatant, and collecting precipitated foxtail millet grains.

Optionally, 100 ml of the induction culture medium, for example, can contain: K-buffer 0.8-1.2 ml, M-N solution 1.8-2.2 ml, 1% $CaCl_2$ 0.08-0.12 ml, 0.01% $FeSO_4$ 0.8-1.2 ml, 20% $NH_4NO_3$ 0.23-0.27 ml, Spore elements 0.48-0.52 ml, 50% glycerol 0.8-1.2 ml, 1 mol/L pH5.3 MES 3.8-4.2 ml and 2 mol/L dextrose 0.48-0.52 ml.

In some preferred embodiments, 100 ml of the induction culture medium for example can contain: K-buffer 1 ml, M-N solution 2 ml, 1% $CaCl_2$ 0.01 ml, 0.01% $FeSO_4$ 1 ml, 20% $NH_4NO_3$ 0.25 ml, Spore elements 0.5 ml, 50% glycerol 1 ml, 1 mol/L pH5.3 MES 4 ml and 2 mol/L dextrose 0.5 ml.

Optionally, 100 ml of the above K-buffer can contain: $K_2HPO_4$ 18-22 g and $KH_2PO_4$ 14-15 g. A pH value of the above K-buffer, for example, can be 6.8-7.2. In some preferred embodiments, 100 ml of the K-buffer can contain: $K_2HPO_4$ 20 g and $KH_2PO_4$ 14.5 g, and the pH value of the K-buffer in this condition is 7.0.

Optionally, 100 ml of the above M-N solution can contain: $MgSO_4 \cdot 7H_2O$ 2.8-3.2 g and NaCl 1.3-1.7 g. In some preferred embodiments, 100 ml of the M-N solution can contain: $MgSO_4 \cdot 7H_2O$ 3 g and NaCl 1.5 g.

Optionally, the Spore elements can be obtained by mixing 450-550 mg/L $ZnSO_4 \cdot 7H_2O$, 450-550 mg/L $CuSO_4 \cdot 5H_2O$, 450-550 mg/L $H_3BO_3$, 450-550 mg/L $MnSO_4 \cdot H_2O$ and 450-550 mg/L $NaMoO_4 \cdot 2H_2O$ with equal volume proportions.

Preferably, the above Spore elements can be obtained by mixing 500 mg/L $ZnSO_4 \cdot 7H_2O$, 500 mg/L $CuSO_4 \cdot 5H_2O$, 500 mg/L $H_3BO_3$, 500 mg/L $MnSO_4 \cdot H_2O$ and 500 mg/L $NaMoO_4 \cdot 2H_2O$ with equal volume proportions.

Optionally, in the above Step (b), a mass volume ratio (g:ml) of the foxtail millet grains to the induction culture medium can be 1:1.3-1.7, for example, 1:1.3, 1:1.4, 1:1.5, 1:1.6 and 1:1.7, preferably 1:1.5.

Optionally, in the above Step (b), the ultrasonic treatment can be carried out under a frequency of 40-60 KHz and a power of 140-160 W for 1 min-2 min, and the soaking treatment can last for 10-15 min.

In some preferred embodiments, in the above Step (b), the ultrasonic treatment can be carried out under a frequency of 50 KHz and a power of 150 W for 1.5 min, and the soaking treatment can last for 12.5 min.

Step (c): mixing the foxtail millet grains obtained in Step (b) with an *agrobacterium* infection liquid containing target genes, performing ultrasonic treatment and static infection, absorbing redundant *agrobacterium* bacterial liquid for removal, and performing co-culturing in a condition of 20-25° C., wherein the foxtail millet grains are shaken up every day during the co-culturing, for example, the foxtail millet grains can be shaken up twice every day.

Optionally, the above *agrobacterium* infection liquid can be obtained in a manner as follows, but not limited to the following: carrying out streak inoculation for *agrobacterium* containing a binary expression vector on a solid culture medium containing corresponding antibiotics, and culturing the *agrobacterium* at 28° C. for 2-3 days; then picking single colonies to inoculate them in a liquid culture medium for culturing at 28° C. and 180-220 r/min until $OD_{600}$=0.5-0.6; then re-suspending the *agrobacterium* bacterial liquid in the induction culture medium for culturing at 28° C. and 180-220 r/min until $OD_{600}$=0.5-0.6, to obtain the *agrobacterium* infection liquid that can be used for infection.

Optionally, the above *agrobacterium* for example can contain a binary expression vector pYN6981 (containing target gene EGFP). The antibiotics can contain 20 mg/L rifampin (rif) and 50 mg/L kanamycin (Kan).

Optionally, the solid culture medium can be an LB solid culture medium. 1 L of the LB solid culture medium for example can contain: tryptone 10 g, yeast extract 5 g, sodium chloride 10 g and agar 15 g.

The liquid culture medium can be an LB liquid culture medium. 1 L of the LB liquid culture medium for example can contain: tryptone 10 g, yeast extract 5 g and sodium chloride 10 g.

In a specific embodiment, re-suspending of the *agrobacterium* bacterial liquid in the induction culture medium can include: re-suspending 200 μl of the *agrobacterium* bacterial liquid obtained above in 5 mL of the induction culture medium, wherein acetosyringone (AS) is added to the induction culture medium to 200 μmol/L.

Preferably, an amount of the *agrobacterium* infection liquid used in Step (c) is identical to an amount of the induction culture medium used in Step (b), that is, a mass volume ratio (g:ml) of the foxtail millet grains to the *agrobacterium* infection liquid can be 1:1.3-1.7, for example, 1:1.3, 1:1.4, 1:1.5, 1:1.6 and 1:1.7, preferably 1:1.5.

Reference can be made to the induction culture medium in Step (b) for the induction culture medium involved in Step (c).

Optionally, in the above Step (c), the ultrasonic treatment can be carried out under a frequency of 40-60 KHz and a power of 140-160 W for 10 s-30 s, and the static infection can last for 20-30 min.

In some preferred embodiments, in the above Step (c), the ultrasonic treatment can be carried out under a frequency of 45 KHz and a power of 150 W for 20 s, and the static infection can last for 25 min.

Step (d): picking, after the co-culturing has ended, individual foxtail millet grains and transferring them to a screening culture medium, and performing screening culturing in a condition of 20-25° C.

Optionally, 1 L of the above screening culture medium can for example contain: potato 190-210 g, dextrose 18-22 g and agar powder 18-22 g.

Besides, a method for genetic transformation of enoki mushroom in the present disclosure can include following steps:

(1) transferring enoki mushroom mycelia cultured on a solid culture medium, together with the culture medium, into a homogenizer, adding a liquid culture medium, and intermittently smashing them to obtain liquid mycelia; then inoculating the liquid mycelia into a foxtail-millet-grain culture medium for culturing at 20-25° C. for 8-10 days, shaking up every day during the culturing until the foxtail millet grains become white.

Optionally, the above solid culture medium can be a potato-dextrose-agar (PDA) culture medium, the culture medium transferred to the homogenizer can have a size of (45-55) mm×(45-55) mm, preferably 50 mm×50 mm, and the liquid culture medium can be a potato-dextrose-broth (PDB) culture medium.

Optionally, preferably, enoki mushroom mycelia cultured on the potato-dextrose-agar culture medium for 6-8 days (preferably 7 days), together with the culture medium, are transferred into the homogenizer, and 80-120 ml (preferably, 100 ml) of the potato-dextrose-broth culture medium is added.

Optionally, the intermittent smashing for example can last for 25-35 s, preferably 30 s.

Optionally, the foxtail-millet-grain culture medium can be prepared through a following method: cleaning the foxtail millet grains, soaking the foxtail millet grains with distilled water for 18-30 min to make the foxtail millet grains become slightly soft, dispersing the foxtail millet grains on a gauze for absorbing moisture, then placing the foxtail millet grains into a triangular flask, and carrying out high-temperature high-pressure sterilization.

Optionally, the above soaking can last for 18-22 min, for example 18 min, 20 min and 22 min, and the high-temperature high-pressure sterilization can be carried out in a condition of 120° C. for 28-32 min, for example, 28 min, 30 min and 32 min.

(2) carrying out streak inoculation for *agrobacterium* containing a binary expression vector on a solid culture medium containing corresponding antibiotics, and culturing the *agrobacterium* at 28° C. for 2-3 days; then picking single colonies to inoculate them in the liquid culture medium for culturing at 28° C. and 180-220 r/min until $OD_{600}$=0.5-0.6; and then re-suspending the *agrobacterium* bacterial liquid in the induction culture medium for culturing at 28° C. and 180-220 r/min until $OD_{600}$=0.5-0.6.

Optionally, the above *agrobacterium* for example can contain a binary expression vector GpiE, and the antibiotics can contain 20 mg/L rifampin (rif) and 50 mg/L kanamycin (Kan).

Optionally, the solid culture medium can be an LB solid culture medium. 1 L of the LB solid culture medium for example can contain: tryptone 10 g, yeast extract 5 g, sodium chloride 10 g and agar 15 g.

The liquid culture medium can be an LB liquid culture medium. 1 L of the LB liquid culture medium for example can contain: tryptone 10 g, yeast extract 5 g and sodium chloride 10 g.

In a specific embodiment, re-suspending of the *agrobacterium* bacterial liquid in the induction culture medium can includes: re-suspending 200 μl of the *agrobacterium* bacterial liquid obtained above in 5 mL of the induction culture medium, wherein acetosyringone (AS) is added to the induction culture medium to 200 μmol/L.

Optionally, a formula of the above induction culture medium for example can contain: K-buffer 0.8-1.2 ml, M-N solution 1.8-2.2 ml, 1% $CaCl_2$ 0.08-0.12 ml, 0.01% $FeSO_4$ 0.8-1.2 ml, 20% $NH_4NO_3$ 0.23-0.27 ml, Spore elements 0.48-0.52 ml, 50% glycerol 0.8-1.2 ml, 1 mol/L pH5.3 MES 3.8-4.2 ml and 2 mol/L dextrose 0.48-0.52 ml, and they are diluted with sterile $ddH_2O$ to 100 ml.

In some preferred embodiments, a formula of the above induction culture medium for example can contain: K-buffer 1 ml, M-N solution 2 ml, 1% $CaCl_2$) 0.01 ml, 0.01% FeSO4 1 ml, 20% NH4NO3 0.25 ml, Spore elements 0.5 ml, 50% glycerol 1 ml, 1 mol/L pH5.3 MES 4 ml and 2 mol/L dextrose 0.5 ml, and they are diluted with sterile ddH2O to 100 ml.

Optionally, the above K-buffer can contain: K2HPO4 18-22 g and KH2PO4 14-15 g, and the K-buffer can be prepared by mixing K2HPO4 and KH2PO4 according to the above formula, then adjusting a pH value to 6.8-7.2 with KOH, and diluting with sterile ddH2O to 100 ml.

In some preferred embodiments, the above K-buffer can contain: $K_2HPO_4$ 20 g and $KH_2PO_4$ 14.5 g, and the K-buffer can be prepared by mixing $K_2HPO_4$ and $KH_2PO_4$ according to the above formula, then adjusting a pH value to 7.0 with KOH, and diluting with sterile $ddH_2O$ to 100 ml.

Optionally, the above M-N solution can contain: $MgSO_4.7H_2O$ 2.8-3.2 g and NaCl 1.3-1.7 g.

In some preferred embodiments, the M-N solution can contain: $MgSO_4.7H_2O$ 3 g and NaCl 1.5 g. In use, $MgSO_4.7H_2O$ and NaCl are mixed according to the above formula, then they are diluted with sterile $ddH_2O$ to 100 ml.

Optionally, the above Spore elements can be obtained by mixing 450-550 mg/L $ZnSO_4.7H_2O$, 450-550 mg/L $CuSO_4.5H_2O$, 450-550 mg/L $H_3BO_3$, 450-550 mg/L $MnSO_4.H_2O$ and 450-550 mg/L $NaMoO_4.2H_2O$ with equal volume proportions.

In some preferred embodiments, the above Spore elements can be obtained by mixing 500 mg/L $ZnSO_4.7H_2O$, 500 mg/L $CuSO_4.5H_2O$, 500 mg/L $H_3BO_3$, 500 mg/L $MnSO_4.H_2O$ and 500 mg/L $NaMoO_4.2H_2O$ with equal volume proportions.

(3) adding the foxtail millet grains of Step (1) to a container, adding an induction culture medium, performing ultrasonic treatment and soaking treatment, and removing a supernatant by absorption, wherein the induction culture medium in Step (3) is identical to the induction culture medium in Step (2).

Optionally, a ratio of the foxtail millet grains to the induction culture medium to the *agrobacterium* bacterial liquid added in Step (3) for example can be 1 g:(1.3-1.7) ml:(1.3-1.7) ml. Preferably, the ratio of the them added is 1 g:1.5 ml:1.5 ml.

Optionally, in Step (3), the ultrasonic treatment can be carried out under a frequency of 40-60 KHz and a power of 140-160 W for 1 min-2 min, and the soaking can last for 10-15 min.

(4) adding the *agrobacterium* bacterial liquid of Step (2) to Step (3), performing ultrasonic treatment and static infection, absorbing redundant bacterial liquid for removal, and performing culturing in a condition of 20-25° C. for 72 hours or more, wherein shaking is performed every day during the culturing; finally, picking individual foxtail millet grains and transferring them to induction culture medium plates for culturing at 20-25° C. for 7-10 days.

Optionally, in Step (4), the ultrasonic treatment can be carried out under a frequency of 40-60 KHz and a power of 140-160 W for 10 s-20 s, and the static infection can last for 20-30 min.

The induction culture medium plates in Step (4) for example can contain 5 mg/L hygromycin (Hyg), 400 mg/L cefotaxime sodium (cef), and 200 μmol/L AS.

Besides, a method for genetic transformation of shiitake in the present disclosure can include following steps:

(1) transferring shiitake mycelia cultured on a solid culture medium, together with the culture medium, into a homogenizer, adding a liquid culture medium, and intermittently smashing them to obtain liquid mycelia; then inoculating the liquid mycelia into a foxtail-millet-grain culture medium for culturing at 20-25° C. for 15-20 days, wherein skaking is performed every day during the culturing until the foxtail millet grains become white.

Optionally, the above solid culture medium can be a potato-dextrose-agar (PDA) culture medium, the culture medium transferred to the homogenizer can have a size of (45-55) mm×(45-55) mm, preferably 50 mm×50 mm, and the liquid culture medium can be a potato-dextrose-broth (PDB) culture medium.

Optionally, preferably, enoki mushroom mycelia cultured on the potato-dextrose-agar culture medium for 6-8 days (preferably 7 days), together with the culture medium, are transferred into a homogenizer, and 80-120 ml (preferably, 100 ml) of the potato-dextrose-broth culture medium is added.

Optionally, the intermittent smashing for example can last for 25-35 s, preferably 30 s.

Optionally, the foxtail-millet-grain culture medium can be prepared through a following method: cleaning the foxtail millet grains, soaking the foxtail millet grains with distilled water for 18-30 min to make the foxtail millet grains become slightly soft, dispersing the foxtail millet grains on a gauze for absorbing moisture, then placing the foxtail millet grains into a triangular flask, and carrying out high-temperature high-pressure sterilization.

Optionally, the above soaking can last for 18-22 min, for example 18 min, 20 min and 22 min, and the high-temperature high-pressure sterilization can be carried out in a condition of 120° C. for 28-32 min, for example, 28 min, 30 min and 32 min.

(2) carrying out streak inoculation for *agrobacterium* containing a binary expression vector on a solid culture medium containing corresponding antibiotics, culturing the *agrobacterium* at 28° C. for 2-3 days; then picking single colonies to inoculate them in the liquid culture medium for culturing at 28° C. and 180-220 r/min until OD600=0.5-0.6; and then re-suspending the *agrobacterium* bacterial liquid in the induction culture medium for culturing at 28° C. and 180-220 r/min until OD600=0.5-0.6.

Optionally, the above *agrobacterium* for example can contain a binary expression vector GpiE, and the antibiotics can contain 20 mg/L rifampin (rif) and 50 mg/L kanamycin (Kan).

Optionally, the solid culture medium can be an LB solid culture medium. 1 L of the LB solid culture medium for example can contain: tryptone 10 g, yeast extract 5 g, sodium chloride 10 g and agar 15 g.

The liquid culture medium can be an LB liquid culture medium. 1 L of the LB liquid culture medium for example can contain: tryptone 10 g, yeast extract 5 g and sodium chloride 10 g.

In a specific embodiment, re-suspending of the *agrobacterium* bacterial liquid in the induction culture medium can include: re-suspending 200 μl of the *agrobacterium* bacterial liquid obtained above in 5 mL of the induction culture medium, wherein acetosyringone (AS) is added to the induction culture medium to 200 μmol/L.

Optionally, a formula of the above induction culture medium for example can contain: K-buffer 0.8-1.2 ml, M-N solution 1.8-2.2 ml, 1% $CaCl_2$ 0.08-0.12 ml, 0.01% $FeSO_4$ 0.8-1.2 ml, 20% $NH_4NO_3$ 0.23-0.27 ml, Spore elements 0.48-0.52 ml, 50% glycerol 0.8-1.2 ml, 1 mol/L pH5.3 MES 3.8-4.2 ml and 2 mol/L dextrose 0.48-0.52 ml, and they are diluted with sterile $ddH_2O$ to 100 ml.

In some preferred embodiments, a formula of the above induction culture medium for example can contain: K-buffer 1 ml, M-N solution 2 ml, 1% $CaCl_2$ 0.01 ml, 0.01% $FeSO_4$ 1 ml, 20% $NH_4NO_3$ 0.25 ml, Spore elements 0.5 ml, 50% glycerol 1 ml, 1 mol/L pH5.3 MES 4 ml and 2 mol/L dextrose 0.5 ml, and they are diluted with sterile $ddH_2O$ to 100 ml.

Optionally, the above K-buffer can contain: K2HPO4 18-22 g and KH2PO4 14-15 g, and the K-buffer can be prepared by mixing K2HPO4 and KH2PO4 according to the above formula, then adjusting a pH value to 6.8-7.2 with KOH, and diluting with sterile ddH2O to 100 ml.

In some preferred embodiments, the above K-buffer can contain: K2HPO4 20 g and KH2PO4 14.5 g, and the K-buffer can be prepared by mixing K2HPO4 and KH2PO4 according to the above formula, then adjusting a pH value to 7.0 with KOH, and diluting with sterile ddH2O to 100 ml.

Optionally, the above M-N solution can contain: MgSO4.7H2O 2.8-3.2 g and NaCl 1.3-1.7 g. In some preferred embodiments, the M-N solution can contain: MgSO4.7H2O 3 g and NaCl 1.5 g. In use, MgSO4.7H2O and NaCl are mixed according to the above formula, then they are diluted with sterile ddH2O to 100 ml.

Optionally, the above Spore elements can be obtained by mixing 450-550 mg/L ZnSO4.7H2O, 450-550 mg/L CuSO4.5H2O, 450-550 mg/L H3BO3, 450-550 mg/L MnSO4.H2O and 450-550 mg/L NaMoO4.2H2O with equal volume proportions.

In some preferred embodiments, the above Spore elements can be obtained by mixing 500 mg/L $ZnSO_4.7H_2O$, 500 mg/L $CuSO_4.5H_2O$, 500 mg/L $H_3BO_3$, 500 mg/L $MnSO_4.H_2O$ and 500 mg/L $NaMoO_4.2H_2O$ with equal volume proportions.

(3) adding the foxtail millet grains in Step (1) to a container, adding an induction culture medium, performing ultrasonic treatment and soaking treatment, and removing a supernatant by absorption, wherein the ultrasonic treatment can be carried out under a frequency of 40-60 KHz and a power of 140-160 W for 1 min-2 min, and the soaking can last for 10-15 min.

The induction culture medium in Step (3) is identical to the induction culture medium in Step (2).

Optionally, a ratio of the foxtail millet grains to the induction culture medium to the *agrobacterium* bacterial liquid added in Step (3) for example can be 1 g:(1.3-1.7) ml:(1.3-1.7) ml. Preferably, the ratio of the them added is 1 g:1.5 ml:1.5 ml.

Optionally, in Step (3), the ultrasonic treatment can be carried out under a frequency of 40-60 KHz and a power of 140-160 W for 1 min-2 min, and the soaking can last for 10-15 min.

(4) adding the *agrobacterium* bacterial liquid of Step (2) to Step (3), performing ultrasonic treatment and static infection, absorbing redundant *agrobacterium* bacterial liquid for removal, and performing culturing in a condition of 20-25° C. for 72 hours or more, wherein shaking is performed every day during the culturing; finally, picking individual foxtail millet grains and transferring them to induction culture medium plates for culturing at 20-25° C. for 7-10 days.

Optionally, in Step (4), the ultrasonic treatment can be carried out under a frequency of 40-60 KHz and a power of 140-160 W for 10 s-20 s, and the static infection can last for 20-30 min.

The induction culture medium and the plates in Step (4) for example can contain 5 mg/L hygromycin (Hyg), 400 mg/L cefotaxime sodium (cef) and 200 μmol/LAS.

The features and performances of the present disclosure are further described below in detail in combination with examples.

Example 1

A method for genetic transformation of *Agaricus bisporus* provided in the present example included following steps:

1. Preparation of a Foxtail-Millet-Grain Culture Medium 1.1 Foxtail millets were cleaned, soaked with distilled water for 20 minutes until the foxtail millets become slightly soft, and dispersed on a clean gauze for absorbing moisture.

1.2 30 g of foxtail millet grains were weighed, placed into a triangular flask of 250 ml, and subjected to high-temperature high-pressure sterilization (120° C., 30 min), to obtain a foxtail-millet-grain culture medium.

2. Preparation of *Agaricus bisporus* Liquid Mycelia

*Agaricus bisporus* monokaryon s73 mycelia cultured on a potato-dextrose-agar (PDA) culture medium for 20 days, together with the culture medium (50 mm×50 mm) were transferred into a homogenizer, 100 ml of a potato-dextrose-broth (PDB) culture medium was added, and they were intermittently smashed for 30 s to obtain *Agaricus bisporus* liquid mycelia.

3. Preparation of an *Agrobacterium* Infection Liquid 3.1 *Agrobacterium* containing a binary expression vector pYN6981 (containing target gene EGFP) was subjected to streak inoculation on LB solid culture medium containing corresponding antibiotics (20 mg/L rifampicin (rif), 50 mg/L kanamycin (Kan)), for culturing at 28° C. for 2 days.

In the above, 1 L of the LB solid culture medium contained: tryptone 10 g, yeast extract 5 g, sodium chloride 10 g, and agar 15 g.

3.2 Single colonies were picked and inoculated into 5 mL of an LB liquid culture medium (containing 20 mg/L rifampicin (rif), 50 mg/L kanamycin (Kan)) for culturing at 28° C. and 200 r/min until OD600=0.5-0.6.

In the above, 1 L of an LB liquid culture medium formula contains: tryptone 10 g, yeast extract 5 g, and sodium chloride 10 g.

3.3 200 μl of the *agrobacterium* bacterial liquid obtained in Step 3.2 was re-suspended in 5 mL of an induction culture medium (with addition of 200 μmol/L acetosyringone AS), for culturing at 28° C. and 200 r/min until OD600=0.5-0.6, to obtain an *agrobacterium* infection liquid.

In the above, 100 ml of the induction culture medium was prepared through a following method: mixing K-buffer 1 ml, M-N solution 2 ml, 1% $CaCl_2$) 0.1 ml, 0.01% FeSO4 1 ml, 20% NH4NO3 0.25 ml, Spore elements 0.5 ml, 50% glycerol 1 ml, 1 mol/L pH5.3 MES 4 ml and 2 mol/L dextrose 0.5 ml, and diluting them with ddH2O to 100 ml.

In the above, 100 ml of the K-buffer was prepared through a following method: mixing K2HPO4 20 g and KH2PO4 14.5 g, adjusting a pH value to 7.0 with KOH, and diluting them with sterile ddH2O to 100 ml.

100 ml of the M-N solution was prepared through a following method: mixing MgSO4.7H2O 3 g and NaCl 1.5 g, and diluting them with sterile ddH2O to 100 ml.

The Spore elements were obtained through a following method: mixing 500 mg/L ZnSO4.7H2O, 500 mg/L CuSO4.5H2O, 500 mg/L H3BO3, 500 mg/L MnSO4.H2O and 500 mg/L NaMoO4.2H2O with equal volume proportions, filtering and sterilizing, and storing them at 4° C.

4. 10 ml of the *Agaricus bisporus* liquid mycelia obtained in Step 2 was inoculated into the foxtail-millet-grain culture medium for pre-culturing at 25° C., wherein during the culturing, the foxtail-millet-grain culture medium was shaken up (or shaken) every day until *Agaricus bisporus* mycelia grew on surfaces of the foxtail millet grains, to obtain a foxtail millet grain-*Agaricus bisporus* mycelium complex.

5. About 1 g of the cultured foxtail millet grain-*Agaricus bisporus* mycelium complex was added into a glass test tube, added with 1.5 ml of the induction culture medium, subjected to ultrasonic treatment under a frequency of 40 KHz and a power of 160 W with a dual-frequency ultrasonic cleaner of Shanghai Kudos Ultrasonic instrument co., Ltd. for 1 min, and then subjected to static soaking for 10 min. The supernatant was removed by absorption, and the precipitated foxtail millet grains were kept.

6. 1.5 ml of the *agrobacterium* infection liquid was added to the foxtail millet grains in Step 5, subjected to ultrasonic treatment with the dual-frequency ultrasonic cleaner of Shanghai Kudos Ultrasonic instrument co., Ltd. for 10 s (with a frequency of 40 KHz, a power of 160 W), and subjected to static infection for 20 min. The redundant bacterial liquid was removed by absorption, and static co-culturing was performed at 25° C. for 72 hours or more, wherein the grains were shaken up twice every day during the co-culturing.

7. After the co-culturing had ended, foxtail millet grain individuals were picked and transferred to primary-screening culture medium plates for culturing at 25° C. for 10 days, with 20 grains being inoculated on each plate.

8. The mycelia around the foxtail millet grains were re-transferred to a re-screening culture medium, wherein mycelia that were not infected by the *agrobacterium* were disposed in the middle of the plates as control. Culturing was performed at 25° C., and the growth state of the mycelia was observed.

9. Screening and Verification of Transformants

Transformants grown with mycelia on the re-screening culture medium (as shown in FIG. 1) were selected, the mycelia thereof were picked to carry out colony PCR, and the mycelia that passed the PCR verification were selected for storing or subsequent experiments.

Each foxtail millet grain could be used as a separate transformation individual, then the operation and statistics were more quick and convenient, and the separation was also easier (as shown in FIG. 1).

In the above, the primary-screening culture medium and the re-screening culture medium had substantially identical ingredients, and were prepared through a following method: mixing 200 g of potato, 20 g of dextrose and 20 g of agar powder; diluting them with ddH2O to 1 L, performing high-temperature high-pressure sterilization, then adding 5 mg/L hygromycin for the primary-screening culture medium and 10 mg/L hygromycin for the re-screening culture medium, and adding 400 mg/L cefotaxime sodium.

A method for PCR verification was as follows:

(1) Young aerial mycelia were collected for 2-3 times by scrapping on a plate surface using sterilized toothpicks until there were macroscopic mycelium clusters on heads of the toothpicks (mycelium weight<0.001 g). The toothpicks with the mycelium clusters were placed into a small centrifugal tube (200 μL) to which 100 μL of TE buffer was added in advance, and stirred for several times, so that the mycelia were completely dispersed in the centrifugal tube (the toothpicks should not be placed into the centrifugal tube for a too long period of time, otherwise, the volume of a lysate would be affected, and a PCR amplification effect would be affected).

(2) The centrifugal tube was placed in a microwave oven for heating for 1 min 45 s, taken out and placed immediately on ice, repeatedly pipetted with a pipette, so that the mycelia were mixed uniformly. The supernatant was collected for PCR amplification.

(3) A PCR amplification system had a total volume of 20 μL, comprising: 10×PCR buffer 2 μL, 25 mmol/L MgCl2 2 μL, 10 mmol/L dNTP 0.4 μL, 5 U/μL Taq DNA enzyme 0.2 μL, 10 μmol/L forward primer Hyg-F 1 μL and reverse primer Hyg-R 1 μL, supernatant 2 μL, and ddH2O 11.4 μL.

PCR reaction conditions were as follows: 94° C. 5 min; 94° C. 30 seconds, 56° C. 40 seconds, 72° C. 30 seconds, 30 cycles; 72° C. 8 min.

The hygromycin primers used were:

(SEQ ID NO: 1)
Hyg-F: GATGTTGGCGACCTCGTATT;

(SEQ ID NO: 2)
Hyg-R: TCGTTATGTTTATCGGCACTTT;

(4) Sequencing verification for PCR products was performed in Shanghai Jie Li Biotechnology Company.

10. Statistics of a positive transformation rate was performed, and results showed that the positive transformation rate was 42.3%. Positive transformation rate=number of positive transformants/total number of transformants.

11. The mycelia grown on the re-screening culture medium were observed under a laser confocal microscope for EGFP expression situation of a target gene. Results are shown in FIG. 2.

Figure 2:
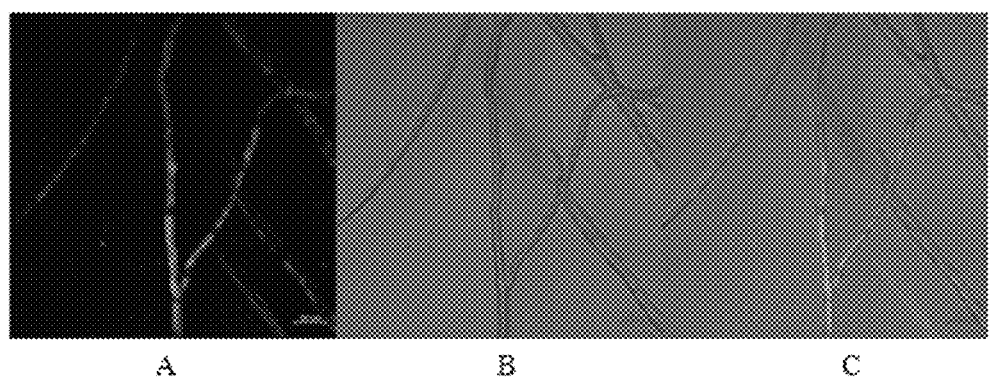
FIG. 2 shows expression results of green fluorescent protein (EGFP) of the transformants in Example 1 of the present disclosure; in the figure: A: green exciting light view; B: white light view; C: superimposed view of the while light view and the exciting light view.

FIG. 2 shows that the mycelia have green fluorescence, indicating that the target gene is successful in EGFP transformation and is successfully expressed in host mycelia.

Example 2

A method for genetic transformation of *Agaricus bisporus* provided in the present example included following steps:

1. Preparation of a Foxtail-Millet-Grain Culture Medium 1.1 Foxtail millets were cleaned, soaked with distilled water for 18 minutes until the foxtail millets become slightly soft, and dispersed on a clean gauze for absorbing moisture.

1.2 30 g of the foxtail millet grains were weighed, placed into a triangular flask of 250 ml, and subjected to high-temperature high-pressure sterilization (120° C., 28 min), to obtain a foxtail-millet-grain culture medium.

2. Preparation of *Agaricus bisporus* Liquid Mycelia

*Agaricus bisporus* monokaryon s73 mycelia cultured on a potato-dextrose-agar (PDA) culture medium for 18 days, together with the culture medium (45 mm×45 mm), were transferred into a homogenizer, 80 ml of a potato-dextrose-broth (PDB) culture medium was added, and they were intermittently smashed for 25 s to obtain *Agaricus bisporus* liquid mycelia.

3. Preparation of an *Agrobacterium* Infection Liquid 3.1 *Agrobacterium* containing a binary expression vector pYN6981 (containing target gene EGPF) was subjected to streak inoculation on LB solid culture medium containing corresponding antibiotics (20 mg/L rifampicin (rif), 50 mg/L kanamycin (Kan)), for culturing at 28° C. for 3 days.

In the above, 1 L of the LB solid culture medium contained: tryptone 10 g, yeast extract 5 g, sodium chloride 10 g and agar 15 g.

3.2 Single colonies were picked and inoculated into 5 mL of an LB liquid culture medium (containing 20 mg/L rifampicin rif, 50 mg/L kanamycin Kan) for culturing at 28° C. and 180 r/min until $OD_{600}$=0.5-0.6.

In the above, 1 L of an LB liquid culture medium formula contained: tryptone 10 g, yeast extract 5 g, and sodium chloride 10 g.

3.3 200 μl of the *agrobacterium* bacterial liquid obtained in Step 3.2 was re-suspended in 5 mL of an induction culture medium (with addition of 200 μmol/L acetosyringone AS), for culturing at 28° C. and 180 r/min until OD600=0.5-0.6, to obtain the *agrobacterium* infection liquid.

In the above, 100 ml of the induction culture medium was prepared through a following method: mixing K-buffer 0.8 ml, M-N solution 1.8 ml, 1% $CaCl_2$ 0.08 ml, 0.01% $FeSO_4$ 0.8 ml, 20% $NH_4NO_3$ 0.23 ml, Spore elements 0.48 ml, 50% glycerol 0.8 ml, 1 mol/L pH5.3 MES 3.8 ml and 2 mol/L dextrose 0.48 ml; and diluting them with $ddH_2O$ to 100 ml.

In the above, 100 ml of the K-buffer was prepared through a following method: mixing K2HPO4 18 g and KH2PO4 14 g, adjusting a pH value to 6.8 with KOH, and diluting them with sterile ddH2O to 100 ml.

100 ml of the M-N solution was prepared through a following method: mixing MgSO4.7H2O 2.8 g and NaCl 1.3 g, and diluting them with sterile ddH2O to 100 ml.

The Spore elements were obtained through a following method: mixing 450 mg/L $ZnSO_4.7H_2O$, 450 mg/L $CuSO_4.5H_2O$, 450 mg/L $H_3BO_3$, 450 mg/L $MnSO_4.H_2O$ and 450 mg/L $NaMoO_4.2H_2O$ with equal volume proportions, filtering and sterilizing, and storing them at 4° C.

4. 10 ml of the *Agaricus bisporus* liquid mycelia obtained in Step 2 was inoculated into the foxtail-millet-grain culture medium for pre-culturing at 20° C., wherein during the culturing, the foxtail-millet-grain culture medium was shaken up (or shaken) every day until the *Agaricus bisporus* mycelia grew on surfaces of the foxtail millet grains, to obtain a foxtail millet grain-*Agaricus bisporus* mycelium complex.

5. About 1 g of the cultured foxtail millet grain-*Agaricus bisporus* mycelium complex was added into a glass test tube, added with 1.3 ml of the induction culture medium, subjected to ultrasonic treatment under a frequency of 50 KHz and a power of 150 W with a dual-frequency ultrasonic cleaner of Shanghai Kudos Ultrasonic instrument co., Ltd. for 1.5 min, and then subjected to static soaking for 12.5 min. The supernatant was removed by absorption, and the precipitated foxtail millet grains were kept.

6. 1.3 ml of the *agrobacterium* infection liquid was added to the foxtail millet grains in Step 5, subjected to ultrasonic treatment with the dual-frequency ultrasonic cleaner of Shanghai Kudos Ultrasonic instrument co., Ltd. for 20 s (with a frequency of 45 KHz, a power of 150 W), and subjected to static infection for 25 min. The redundant bacterial liquid was removed by absorption, and static co-culturing was performed at 25° C. for 72 hours or more, wherein shaking was performed twice every day during the co-culturing.

7. After the co-culturing had ended, foxtail millet grain individuals were picked and transferred to primary-screening culture medium plates for culturing at 20° C. for 9 days, with 20 grains being inoculated on each plate.

8. The mycelia around the foxtail millet grains were re-transferred to a re-screening culture medium, wherein mycelia that were not infected by the *agrobacterium* were disposed in the middle of the plates as control. Culturing was performed at 20° C., and the growth state of the mycelia was observed.

Example 3

A method for genetic transformation of *Agaricus bisporus* provided in the present example included following steps:

1. Preparation of a Foxtail-Millet-Grain Culture Medium 1.1. Foxtail millets were cleaned, soaked with distilled water for 22 minutes until the foxtail millets become slightly soft, and dispersed on a clean gauze for absorbing moisture.

1.2. 30 g of foxtail millet grains were weighed, placed into a triangular flask of 250 ml, and subjected to high-temperature high-pressure sterilization (120° C., 32 min), to obtain a foxtail-millet-grain culture medium.

2. Preparation of *Agaricus bisporus* Liquid Mycelia

*Agaricus bisporus* monokaryon s73 mycelia cultured on a potato-dextrose-agar (PDA) culture medium for 22 days, together with the culture medium (55 mm×55 mm), were transferred into a homogenizer, 120 ml of a potato-dextrose-broth (PDB) culture medium was added, and they were intermittently smashed for 35 s to obtain *Agaricus bisporus* liquid mycelia.

3. Preparation of an *Agrobacterium* Infection Liquid 3.1 *Agrobacterium* containing a binary expression vector pYN6981 (containing target gene EGFP) was subjected to streak inoculation on LB solid culture medium containing corresponding antibiotics (20 mg/L rifampicin rif, 50 mg/L kanamycin Kan), for culturing at 28° C. for 2.5 days.

In the above, 1 L of an LB solid culture medium contained: tryptone 10 g, yeast extract 5 g, sodium chloride 10 g and agar 15 g.

3.2 Single colonies were picked and inoculated into 5 mL of an LB liquid culture medium (containing 20 mg/L rifampicin rif, 50 mg/L kanamycin Kan) for culturing at 28° C. and 220 r/min until OD600=0.5-0.6.

In the above, 1 L of an LB liquid culture medium formula contained: tryptone 10 g, yeast extract 5 g, and sodium chloride 10 g.

3.3 200 μl of the *agrobacterium* bacterial liquid obtained in Step 3.2 was re-suspended in 5 mL of an induction culture medium (with addition of 200 μmol/L acetosyringone AS), for culturing at 28° C. and 220 r/min until OD600=0.5-0.6, to obtain an *agrobacterium* infection liquid.

In the above, 100 ml of the induction culture medium was prepared through a following method: mixing K-buffer 1.2 ml, M-N solution 2.2 ml, 1% $CaCl_2$ 0.12 ml, 0.01% $FeSO_4$ 1.2 ml, 20% $NH_4NO_3$ 0.27 ml, Spore elements 0.52 ml, 50% glycerol 1.2 ml, 1 mol/L pH5.3 MES 4.2 ml and 2 mol/L dextrose 0.52 ml; and diluting them with $ddH_2O$ to 100 ml.

In the above, 100 ml of the K-buffer was prepared through a following method: mixing $K_2HPO_4$ 22 g and $KH_2PO_4$ 15 g, adjusting a pH value to 7.2 with KOH, and diluting them with sterile $ddH_2O$ to 100 ml.

100 ml of the M-N solution was prepared through a following method: mixing $MgSO_4 \cdot 7H_2O$ 3.2 g and NaCl 1.7 g, and diluting them with sterile $ddH_2O$ to 100 ml.

The Spore elements were obtained through a following method: mixing 550 mg/L $ZnSO_4 \cdot 7H_2O$, 550 mg/L $CuSO_4 \cdot 5H_2O$, 550 mg/L $H_3BO_3$, 550 mg/L $MnSO_4 \cdot H_2O$ and 550 mg/L $NaMoO_4 \cdot 2H_2O$ with equal volume proportions, filtering and sterilizing, and storing them at 4° C.

4. 10 ml of the *Agaricus bisporus* liquid mycelia obtained in Step 2 was inoculated into the foxtail-millet-grain culture medium for pre-culturing at 22.5° C., wherein during the culturing, the foxtail-millet-grain culture medium was shaken up (or shaken) every day until the *Agaricus bisporus* mycelia grew on surfaces of the foxtail millet grains, to obtain a foxtail millet grain-*Agaricus bisporus* mycelium complex.

5. About 1 g of the cultured foxtail millet grain-*Agaricus bisporus* mycelium complex was added into a glass test tube, added with 1.7 ml of an induction culture medium, subjected to ultrasonic treatment under a frequency of 60 KHz and a power of 140 W with a dual-frequency ultrasonic cleaner of Shanghai Kudos Ultrasonic instrument co., Ltd. for 2 min, and then subjected to static soaking for 15 min. The supernatant was removed by absorption, and the precipitated foxtail millet grains were kept.

6. 1.7 ml of the *agrobacterium* infection liquid was added to the foxtail millet grains in Step 5, subjected to ultrasonic treatment with the dual-frequency ultrasonic cleaner of Shanghai Kudos Ultrasonic instrument co., Ltd. for 30 s (with a frequency of 60 KHz, a power of 140 W), and subjected to static infection for 30 min. The redundant bacterial liquid was removed by absorption, and static co-culturing was performed at 25° C. for 72 hours or more, wherein shaking was performed twice every day during the co-culturing.

7. After the co-culturing had ended, foxtail millet grain individuals were picked and transferred to primary-screening culture medium plates for culturing at 22.5° C. for 8 days, with 20 grains being inoculated on each plate.

8. The mycelia around the foxtail millet grains were re-transferred to a re-screening culture medium, wherein mycelia that were not infected by the *agrobacterium* were disposed in the middle of the plates as control. Culturing was performed at 25° C., and the growth state of the mycelia was observed.

Example 4

A method for genetic transformation of enoki mushroom provided in the present example included following steps:

1. Preparation of a Foxtail-Millet-Grain Culture Medium (1) Foxtail millet grains were cleaned, soaked with distilled water for 20 minutes until the foxtail millets become slightly soft, and dispersed on a clean gauze for absorbing moisture.

(2) 30 g of the foxtail millets were weighed, placed into a triangular flask of 250 ml, and subjected to high-temperature high-pressure sterilization (120° C., 30 min).

2. Inoculation of Enoki Mushroom Mycelia (1) Enoki mushroom mycelia cultured on a potato-dextrose-agar (PDA) culture medium for 7 days, together with the culture medium (50 mm×50 mm), were transferred into a homogenizer, added with 100 ml of a potato-dextrose-broth (PDB) culture medium, and they were intermittently smashed for 30 s.

(2) 10 ml of the above liquid mycelia were inoculated into the foxtail-millet-grain culture medium for culturing at 25° C. for 10 days, wherein shaking was performed every day during the culturing until foxtail millet grains became white.

3. Activated Culturing of *Agrobacterium*

(1) *Agrobacterium* containing a binary expression vector GpiE was subjected to streak inoculation on a LB solid culture medium containing corresponding antibiotics (20 mg/L rifampicin rif, 50 mg/L kanamycin Kan), for culturing at 28° C. for 2 days, wherein the formula of 1 L of the LB solid culture medium contained: tryptone 10 g, yeast extract 5 g, sodium chloride 10 g, and agar 15 g.

(2) Single colonies were picked and inoculated into 5 mL of an LB liquid culture medium (containing 20 mg/L rifampicin rif, 50 mg/L kanamycin Kan) for culturing at 28° C. and 200 r/min until OD600=0.5-0.6, wherein the formula of 1 L of the LB liquid culture medium contained: tryptone 10 g, yeast extract 5 g, and sodium chloride 10 g.

(3) 200 µl of the above *agrobacterium* bacterial liquid was re-suspended in 5 mL of an induction culture medium (with addition of 200 µmol/L acetosyringone AS), for culturing at 28° C. and 200 r/min until $OD_{600}$=0.5-0.6.

A formula of the induction culture medium was: K-buffer 1 ml; M-N solution 2 ml; 1% $CaCl_2$ 0.1 ml; 0.01% $FeSO_4$ 1 ml; 20% $NH_4NO_3$ 0.25 ml; Spore elements 0.5 ml; 50% glycerol 1 ml; 1 mol/L pH5.3 MES 4 ml; 2 mol/L dextrose 0.5 ml; and they were diluted with sterile $ddH_2O$ to 100 ml.

The K-buffer consisted of K2HPO4 20 g and KH2PO4 14.5 g, which were adjusted to a pH value 7.0 with KOH, and diluted with sterile ddH2O to 100 ml.

The M-N solution consisted of $MgSO_4.7H_2O$ 3 g and NaCl 1.5 g, which were diluted with sterile $ddH_2O$ to 100 ml.

The Spore elements consisted of 500 mg/L $ZnSO_4.7H_2O$, 500 mg/L $CuSO_4.5H_2O$, 500 mg/L $H_3BO_3$, 500 mg/L $MnSO_4.H_2O$ and 500 mg/L $NaMoO_4.2H_2O$, which were mixed at equal volume proportions, filtered and sterilized, and stored at 4° C.

4. *Agrobacterium* Infecting Foxtail Millet Grain-Enoki Mushroom Mycelium Matrix (1) About 1 g of the cultured foxtail millet grains were added into a glass test tube, added with 1.5 ml of an induction culture medium (without addition of acetosyringone AS), subjected to ultrasonic treatment (under a frequency of 40 KHz and a power of 160 W) with a dual-frequency ultrasonic cleaner of Shanghai Kudos Ultrasonic instrument co., Ltd. for 1 min, and placed for 10 min. The supernatant was removed by absorption.

Figure 3:
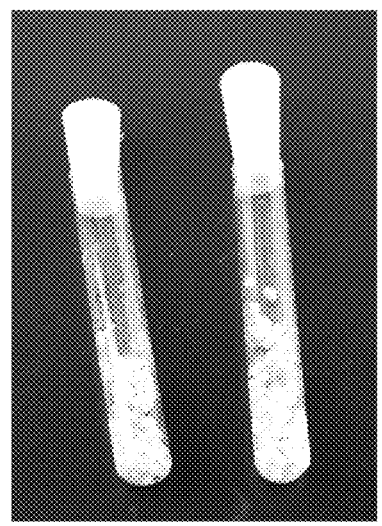
FIG. 3 is a diagram showing static culturing after *agrobacterium* infects a foxtail millet grain-enoki mushroom mycelium matrix in Example 4 of the present disclosure.

(2) 1.5 ml of the *agrobacterium* bacterial liquid well shaken in Step 3 was added, subjected to ultrasonic treatment with the dual-frequency ultrasonic cleaner of Shanghai Kudos Ultrasonic instrument co., Ltd. for 10 s (under a frequency of 40 KHz, a power of 160 W), and subjected to static infection for 20 min. The redundant bacterial liquid was removed by absorption, and static culturing was performed at 25° C. for 72 hours or more, wherein shaking was performed twice every day during the culturing. A growth state thereof is as shown in FIG. 3.

Figure 4:
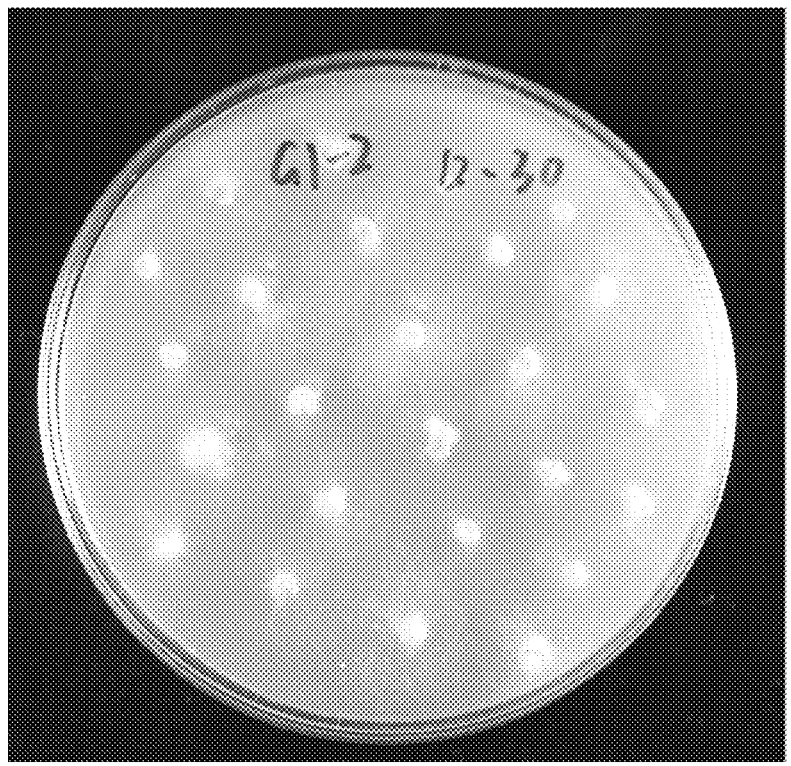
FIG. 4 is a diagram showing a growth state of transformants on an induction culture medium plate in Example 4 of the present disclosure (G1-2 represents a strain number)

(3) The foxtail millet grain individuals were transferred to induction culture medium plates (containing 5 mg/L hygromycin Hyg, 400 mg/L cefotaxime sodium cef, and 200 µmol/L AS), for culturing at 25° C. for 7 days, with 25 grains being inoculated on each plate. A growth state thereof is as shown in FIG. 4.

Figure 5:
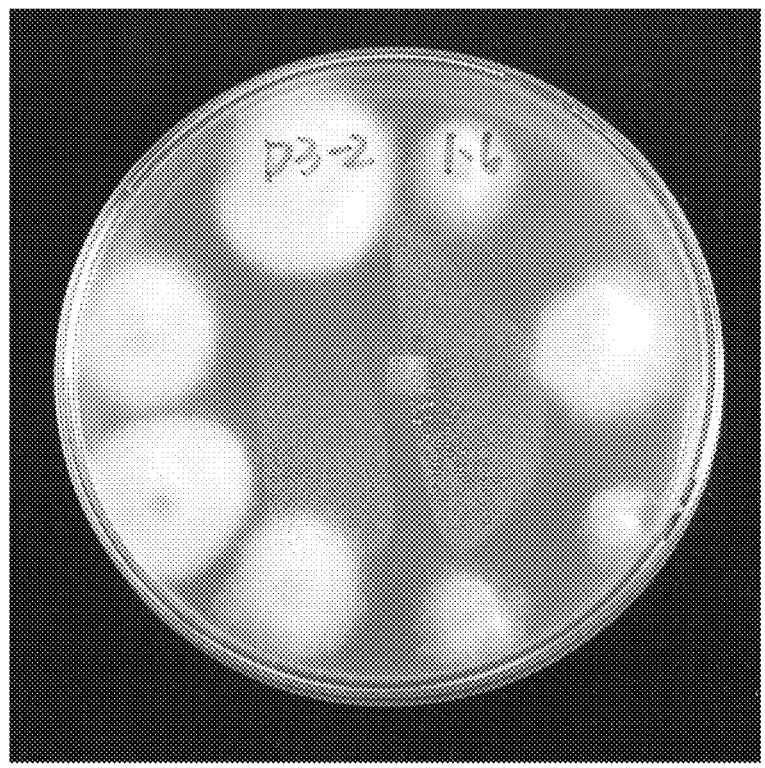
FIG. 5 is a diagram showing a growth state of transformants on a screening culture medium in Example 4 of the present disclosure (a middle bacterium mass is not transformed for control, and D3-2 represents a strain number)

(4) The number of the foxtail millet grains on which the mycelia could grow was counted, and the mycelia around the foxtail millet grains were re-transferred to a screening culture medium (10 mg/L Hyg, 400 mg/L cef), wherein mycelia that were not infected by the *agrobacterium* were disposed in the middle of the plates as control. Culturing was performed at 25° C., and the growth state of the mycelia was observed. Results are as shown in FIG. 5.

5. Screening and Verification of Transformants (1) Transformants on which the mycelia could grow were inoculated into a potato-dextrose-broth culture medium, subjected to shaking culturing in a light-tight condition at 23° C.-25° C., and mycelia were collected after 3 d-4 d.

(2) Genome DNAs of the above mycelia were extracted using a CTAB (hexadecyltrimethylammonium bromide) method, a concentration and a purity of a total genome DNA were detected, and the concentration of sample DNA was adjusted to be consistent with the same.

(3) PCR amplification of marker gene hygromycin Hyg was carried out for the DNAs extracted above.

A PCR amplification system had a total volume of 20 µL, comprising: 10×PCR buffer 2 µL, 25 mmol/L $MgCl_2$ 2 µL, 10 mmol/L dNTP 0.4 µL, 5 U/µL Taq DNA enzyme 0.2 µL, 10 µmol/L Hyg forward primer 1 µL and reverse primer 1 µL, template DNA 2 µL extracted at a concentration of 20 ng-30 ng/µL, and $ddH_2O$ 11.4 µL.

PCR reaction conditions were as follows: 94° C. 5 min; 94° C. 30 seconds, 56° C. 40 seconds, 72° C. 30 seconds, 30 cycles; 72° C. 8 min.

The hygromycin primers used were:

```
                                                (SEQ ID NO: 1)
    Hyg-F: GATGTTGGCGACCTCGTATT;

(SEQ ID NO: 2)
    Hyg-R: TCGTTATGTTTATCGGCACTTT;
```

(4) Sequencing verification for PCR products was performed in Shanghai Jie Li Biotechnology Company.

(5) Statistics of a positive transformation rate was performed, a transformation rate result was 38.26%, and breed conservation was performed.

Example 5

A method for genetic transformation of enoki mushroom provided in the present example included following steps:

1. Preparation of a Foxtail-Millet-Grain Culture Medium (1) Foxtail millets were cleaned, soaked with distilled water for 18 minutes until the foxtail millets become slightly soft, and dispersed on a clean gauze for absorbing moisture.

(2) 30 g of the foxtail millets were weighed, placed into a triangular flask of 250 ml, and subjected to high-temperature high-pressure sterilization (120° C., 28 min).

2. Inoculation of Enoki Mushroom Mycelia (1) Enoki mushroom mycelia cultured on a potato-dextrose-agar (PDA) culture medium for 7 days, together with the culture medium (45 mm×45 mm), were transferred into a homogenizer, added with 100 ml of a potato-dextrose-broth (PDB) culture medium, and they were intermittently smashed for 25 s.

(2) 10 ml of the above liquid mycelia were inoculated into the foxtail-millet-grain culture medium for culturing at 20° C. for 8 days, wherein shaking was performed every day during the culturing until the foxtail millet grains became white.

3. Activated Culturing of *Agrobacterium*

(1) *Agrobacterium* containing a binary expression vector GpiE was subjected to streak inoculation on LB solid culture medium containing corresponding antibiotics (20 mg/L rifampicin rif, 50 mg/L kanamycin Kan), for culturing at 28° C. for 2.5 days, wherein the formula of 1 L of the LB solid culture medium contained: tryptone 10 g, yeast extract 5 g, sodium chloride 10 g, and agar 15 g.

(2) Single colonies were picked and inoculated into 5 mL of an LB liquid culture medium (containing 20 mg/L rifampicin rif, 50 mg/L kanamycin Kan) for culturing at 28° C. and 180 r/min until OD600=0.5-0.6, wherein the formula of 1 L of an LB liquid culture medium contained: tryptone 10 g, yeast extract 5 g, and sodium chloride 10 g.

(3) 200 µl of the above *agrobacterium* bacterial liquid was re-suspended in 5 mL of an induction culture medium (with addition of 200 µmol/L acetosyringone AS), for culturing at 28° C. and 180 r/min until OD600=0.5-0.6.

A formula of the induction culture medium comprises: K-buffer 0.8 ml; M-N solution 1.8 ml; 1% $CaCl_2$) 0.08 ml; 0.01% FeSO4 0.8 ml; 20% NH4NO3 0.23 ml; Spore elements 0.48 ml; 50% glycerol 0.8 ml; 1 mol/L pH5.3 MES 3.8 ml and 2 mol/L dextrose 0.48 ml, which were diluted with sterile ddH2O to 100 ml.

The K-buffer consisted of K2HPO4 18 g and KH2PO4 14 g, which were adjusted to a pH value 6.8 with KOH, and diluted with sterile ddH2O to 100 ml.

The M-N solution consisted of MgSO4.7H2O 2.8 g and NaCl 1.3 g, which were diluted with sterile ddH2O to 100 ml.

The Spore elements consisted of 450 mg/L ZnSO4.7H2O, 450 mg/L CuSO4.5H2O, 450 mg/L of H3BO3, 450 mg/L MnSO4.H2O and 450 mg/L NaMoO4.2H2O which were mixed at equal volume proportions, filtered and sterilized, and stored at 4° C.

4. *Agrobacterium* Infecting a Foxtail Millet Grain-Enoki Mushroom Mycelium Matrix (1) About 1 g of the cultured foxtail millet grains were added into a glass test tube, added with 1.3 ml of the induction culture medium (without addition of acetosyringone AS), subjected to ultrasonic treatment (under a frequency of 60 KHz and a power of 150 W) with a dual-frequency ultrasonic cleaner of Shanghai Kudos Ultrasonic instrument co., Ltd. for 1.5 min, and then was placed for 10 min. The supernatant was removed by absorption.

(2) 1.3 ml of the *agrobacterium* bacterial liquid well shaken in Step 3 was added, subjected to ultrasonic treatment with the dual-frequency ultrasonic cleaner of Shanghai Kudos Ultrasonic instrument co., Ltd. for 20 s (under a frequency of 50 KHz, a power of 150 W), and subjected to static infection for 25 min. The redundant bacterial liquid was removed by absorption, and static culturing was performed at 20° C. for 72 hours or more, wherein shaking was performed twice every day during the culturing.

(3) The foxtail millet grain individuals were transferred to induction culture medium plates (containing 5 mg/L hygromycin Hyg, 400 mg/L cefotaxime sodium cef, and 200 µmol/L AS), for culturing at 20° C. for 10 days, with 25 grains being inoculated on each plate.

Example 6

A method for genetic transformation of enoki mushroom provided in the present example included following steps:

1. Preparation of a Foxtail-Millet-Grain Culture Medium (1) Foxtail millets were cleaned, soaked with distilled water for 22 minutes until the foxtail millets become slightly soft, and dispersed on a clean gauze for absorbing moisture.

(2) 30 g of the foxtail millets were weighed, placed into a triangular flask of 250 ml, and subjected to high-temperature high-pressure sterilization (120° C., 32 min).

2. Inoculation of Enoki Mushroom Mycelia (1) Enoki mushroom mycelia cultured on a potato-dextrose-agar (PDA) culture medium for 7 days, together with the culture medium (55 mm×55 mm), were transferred into a homogenizer, added with 100 ml of a potato-dextrose-broth (PDB) culture medium, and they were intermittently smashed for 35 s.

(2) 10 ml of the above liquid mycelia were inoculated into the foxtail-millet-grain culture medium for culturing at 22.5° C. for 9 days, wherein shaking was performed every day during the culturing until the foxtail millet grains became white.

3. Activated Culturing of *Agrobacterium*

(1) *Agrobacterium* containing a binary expression vector GpiE was subjected to streak inoculation on LB solid culture medium containing corresponding antibiotics (20 mg/L rifampicin rif, 50 mg/L kanamycin Kan), for culturing at 28° C. for 3 days, wherein the formula of 1 L of the LB solid culture medium contained: tryptone 10 g, yeast extract 5 g, sodium chloride 10 g, and agar 15 g.

(2) Single colonies were picked and inoculated into 5 mL of an LB liquid culture medium (containing 20 mg/L rifampicin rif, 50 mg/L kanamycin Kan) for culturing at 28° C. and 220 r/min until OD600=0.5-0.6, wherein the formula of 1 L of the LB liquid culture medium formula contained: tryptone 10 g, yeast extract 5 g, and sodium chloride 10 g.

(3) 200 µl of the above *agrobacterium* bacterial liquid was re-suspended in 5 mL of an induction culture medium (with addition of 200 µmol/L acetosyringone AS), for culturing at 28° C. and 220 r/min until $OD_{600}$=0.5-0.6.

A formula of the induction culture medium was: K-buffer 1.2 ml; M-N solution 2.2 ml; 1% $CaCl_2$) 0.12 ml; 0.01% FeSO4 1.2 ml; 20% NH4NO3 0.27 ml; Spore elements 0.52 ml; 50% glycerol 1.2 ml; 1 mol/L pH5.3 MES 4.2 ml; 2 mol/L dextrose 0.52 ml, which were diluted with sterile ddH2O to 100 ml.

The K-buffer consisted of K2HPO4 22 g and KH2PO4 15 g, which were adjusted to a pH value 7.2 with KOH, and was diluted with sterile ddH2O to 100 ml.

The M-N solution consisted of MgSO4.7H2O 3.2 g and NaCl 1.7 g, which were diluted with sterile ddH2O to 100 ml.

The Spore elements consisted of 550 mg/L $ZnSO_4.7H_2O$, 550 mg/L $CuSO_4.5H_2O$, 550 mg/L $H_3BO_3$, 550 mg/L $MnSO_4.H_2O$ and 550 mg/L $NaMoO_4.2H_2O$ which were mixed at equal volume proportions, filtered and sterilized, and stored at 4° C.

4. *Agrobacterium* Infecting a Foxtail Millet Grain-Enoki Mushroom Mycelium Matrix (1) About 1 g of the cultured foxtail millet grains were added into a glass test tube, added with 1.7 ml of an induction culture medium (without addition of acetosyringone AS), subjected to ultrasonic treatment (under a frequency of 50 KHz and a power of 140 W) with a dual-frequency ultrasonic cleaner of Shanghai Kudos Ultrasonic instrument co., Ltd. for 2 min, and then was placed for 10 min. The supernatant was removed by absorption.

(2) 1.7 ml of the *agrobacterium* bacterial liquid well shaken in Step 3 was added, subjected to ultrasonic treatment with the dual-frequency ultrasonic cleaner of Shanghai Kudos Ultrasonic instrument co., Ltd. for 15 s (under a frequency of 60 KHz, a power of 140 W), and subjected to static infection for 30 min. The redundant bacterial liquid was removed by absorption, and static culturing was performed at 22.5° C. for 72 hours or more, wherein shaking was performed twice every day during the culturing.

(3) The foxtail millet grain individuals were transferred to induction culture medium plates (containing 5 mg/L hygromycin Hyg, 400 mg/L cefotaxime sodium cef, and 200 µmol/L AS), for culturing at 22.5° C. for 8.5 days, with 25 grains being inoculated on each plate.

Example 7

A method for genetic transformation of shiitake provided in the present example included following steps:

1. Preparation of a Foxtail-Millet-Grain Culture Medium
  (1) Foxtail millets were cleaned, soaked with distilled water for 20 minutes until the foxtail millets become slightly soft, and dispersed on a clean gauze for absorbing moisture.
  (2) 30 g of the foxtail millets were weighed, placed into a triangular flask of 250 ml, and subjected to high-temperature high-pressure sterilization (120° C., 30 min).

2. Inoculation of Shiitake Mycelia
  (1) Shiitake mycelia cultured on a potato-dextrose-agar (PDA) culture medium for 7 days, together with the culture medium (50 mm×50 mm), were transferred into a homogenizer, added with 100 ml of a potato-dextrose-broth (PDB) culture medium, and they were intermittently smashed for 30 s.
  (2) 10 ml of the above liquid mycelia were inoculated into the foxtail-millet-grain culture medium for culturing at 25° C. for 25 days, wherein shaking was performed every day during the culturing until the foxtail millet grains became white.

3. Activated Culturing of *Agrobacterium*
  (1) *Agrobacterium* containing binary expression vector GpiE was subjected to streak inoculation on LB solid culture medium containing corresponding antibiotics (20 mg/L rifampicin rif, 50 mg/L kanamycin Kan), for culturing at 28° C. for 2 days, wherein the formula of 1 L of an LB solid culture medium contained: tryptone 10 g, yeast extract 5 g, sodium chloride 10 g, and agar 15 g.
  (2) Single colonies were picked and inoculated into 5 mL of an LB liquid culture medium (containing 20 mg/L rifampicin rif, 50 mg/L kanamycin Kan) for culturing at 28° C. and 200 r/min until $OD_{600}$=0.5-0.6, wherein the formula of 1 L of an LB liquid culture medium contained: tryptone 10 g, yeast extract 5 g, and sodium chloride 10 g.
  (3) 200 μl of the above *agrobacterium* bacterial liquid was re-suspended in 5 mL of the induction culture medium (with addition of 200 μmol/L acetosyringone AS), for culturing at 28° C. and 200 r/min until $OD_{600}$=0.5-0.6.

A formula of the induction culture medium was: K-buffer 1 ml; M-N solution 2 ml; 1% $CaCl_2$ 0.1 ml; 0.01% $FeSO_4$ 1 ml; 20% $NH_4NO_3$ 0.25 ml; Spore elements 0.5 ml; 50% glycerol 1 ml; 1 mol/L pH5.3 MES 4 ml; 2 mol/L dextrose 0.5 ml, which were diluted with sterile $ddH_2O$ to 100 ml.

The K-buffer consisted of $K_2HPO_4$ 20 g and $KH_2PO_4$ 14.5 g, which were adjusted to a pH value 7.0 with KOH, and diluted with sterile $ddH_2O$ to 100 ml.

The M-N solution consisted of $MgSO_4.7H_2O$ 3 g and NaCl 1.5 g, which was diluted with sterile $ddH_2O$ to 100 ml.

The Spore elements consisted of 500 mg/L $ZnSO_4.7H_2O$, 500 mg/L $CuSO_4.5H2O$, 500 mg/L $H_3BO_3$, 500 mg/L $MnSO_4.H_2O$ and 500 mg/L $NaMoO_4.2H_2O$ which were mixed at equal volume proportions, filtered and sterilized, and stored at 4° C.

Figure 6:
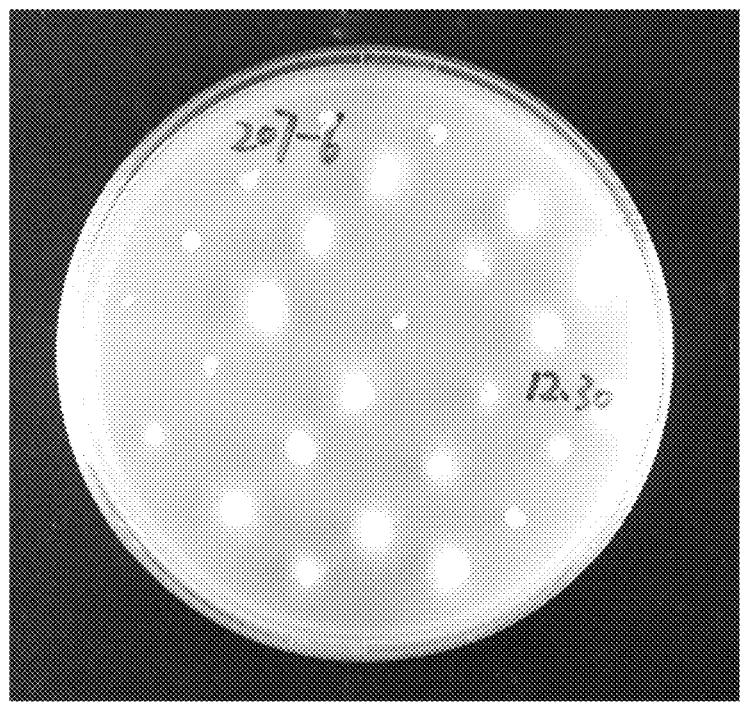
FIG. 6 is a diagram showing a growth state of transformants on an induction culture medium plate in Example 7 of the present disclosure (207-6 represents a strain number)

4. *Agrobacterium* Infecting a Foxtail Millet Grain-Shiitake Mycelium Matrix
  (1) About 1 g of the cultured foxtail millet grains were added into a glass test tube, added with 1.5 ml of the induction culture medium (without addition of acetosyringone AS), subjected to ultrasonic treatment (under a frequency of 40 KHz and a power of 160 W) with a dual-frequency ultrasonic cleaner of Shanghai Kudos Ultrasonic instrument co., Ltd. for 1 min, and then was placed for 10 min. The supernatant was removed by absorption.
  (2) 1.5 ml of the *agrobacterium* bacterial liquid well shaken in Step 3 was added, subjected to ultrasonic treatment with the dual-frequency ultrasonic cleaner of Shanghai Kudos Ultrasonic instrument co., Ltd. for 10 s (under a frequency of 40 KHz, a power of 160 W), and subjected to static infection for 20 min. The redundant bacterial liquid was removed by absorption, and static culturing was performed at 20° C. for 72 hours or more, wherein shaking was performed twice every day during the culturing.
  (3) The foxtail millet grain individuals were transferred to induction culture medium plates (containing 5 mg/L hygromycin Hyg, 400 mg/L cefotaxime sodium cef, and 200 μmol/L AS), for culturing at 25° C. for 10 days, with 25 grains being inoculated on each plate. A growth state thereof was as shown in FIG. 6.
  (4) The number of the foxtail millet grains on which the mycelia could grow was counted, and the mycelia around the foxtail millet grains were re-transferred to a screening culture medium (10 mg/L Hyg, 400 mg/L cef), wherein mycelia that were not infected by the *agrobacterium* were disposed in the middle of the plates as control. Culturing was performed at 25° C., and the growth state of the mycelia was observed. Results showed that all the transformants could grow normally while the control mycelia did not grow.

5. Screening and Verification of Transformants
  (1) Transformants on which the mycelia could grow were inoculated into a potato-dextrose-broth culture medium, subjected to shaking culturing in a light-tight condition at 23° C.–25° C., and mycelia were collected after 3 d-4 d.
  (2) Genome DNAs of the above mycelia were extracted using a CTAB method, a concentration and a purity of a total genome DNA were detected, and the concentration of sample DNAs was adjusted to be consistent with the same.
  (3) PCR amplification of marker gene hygromycin Hyg was carried out for the DNAs extracted above.

A PCR amplification system had a total volume of 20 μL, comprising: 10×PCR buffer 2 μL, 25 mmol/L $MgCl_2$ 2 μL, 10 mmol/L dNTP 0.4 μL, 5 U/μL Taq DNA enzyme 0.2 μL, 10 μmol/L Hyg forward primer 1 μL and reverse primer 1 μL, template DNA 2 μL extracted at a concentration of 20 ng-30 ng/μL, and $ddH_2O$ 11.4 μL.

PCR reaction conditions were as follows: 94° C. 5 min; 94° C. 30 seconds, 56° C. 40 seconds, 72° C. 30 seconds, 30 cycles; 72° C. 8 min.

The hygromycin primers used were:

```
                                                (SEQ ID NO: 1)
       Hyg-F: GATGTTGGCGACCTCGTATT;

(SEQ ID NO: 2)
       Hyg-R: TCGTTATGTTTATCGGCACTTT;
```

Figure 7:
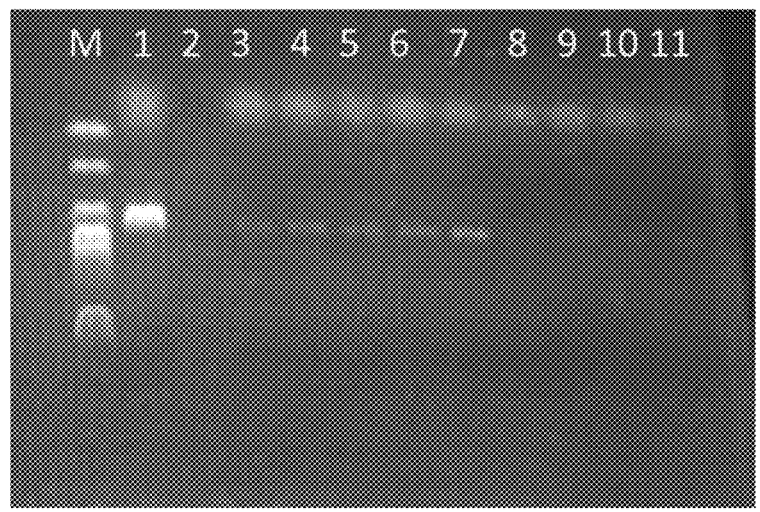
FIG. 7 is a diagram showing PCR (polymerase chain reaction) amplification results of hygromycin primers in Example 7 of the present disclosure, wherein M: DL2000 marker; 1: plasmid used as positive control; 2: non-transformed DNA used as negative control; 3-11: hygromycin amplification of transformants.

Amplification results are as shown in FIG. 7.
  (4) Sequencing verification for PCR products was performed in Shanghai Jie Li Biotechnology Company.
  (5) Statistics of a positive transformation rate was performed, a transformation rate result was 30.17%, and breed conservation was performed.

Example 8

A method for genetic transformation of shiitake provided in the present example included following steps:

1. Preparation of a Foxtail-Millet-Grain Culture Medium
  (1) Foxtail millets were cleaned, soaked with distilled water for 18 minutes until the foxtail millets become slightly soft, and dispersed on a clean gauze for absorbing moisture.

(2) 30 g of the foxtail millets were weighed, placed into a triangular flask of 250 ml, and subjected to high-temperature high-pressure sterilization (120° C., 28 min).

2. Inoculation of Shiitake Mycelia (1) Shiitake mycelia cultured on a potato-dextrose-agar (PDA) culture medium for 7 days, together with the culture medium (45 mm×45 mm), were transferred into a homogenizer, added with 100 ml of a potato-dextrose-broth (PDB) culture medium, and they were intermittently smashed for 25 s.

(2) 10 ml of the above liquid mycelia were inoculated into the foxtail-millet-grain culture medium for culturing at 20° C. for 8 days, wherein shaking was performed every day during the culturing until the foxtail millet grains became white.

3. Activated Culturing of *Agrobacterium*

(1) *Agrobacterium* containing a binary expression vector GpiE was subjected to streak inoculation on LB solid culture medium containing corresponding antibiotics (20 mg/L rifampicin rif, 50 mg/L kanamycin Kan), for culturing at 28° C. for 2.5 days. The formula of 1 L of the LB solid culture medium contained: tryptone 10 g, yeast extract 5 g, sodium chloride 10 g, and agar 15 g.

(2) Single colonies were picked and inoculated into 5 mL of an LB liquid culture medium (containing 20 mg/L rifampicin rif, 50 mg/L kanamycin Kan) for culturing at 28° C. and 180 r/min until OD600=0.5-0.6; 1 L of the LB liquid culture medium formula contained: tryptone 10 g, yeast extract 5 g and sodium chloride 10 g.

(3) 200 μl of the above *agrobacterium* bacterial liquid was re-suspended in 5 mL of the induction culture medium (with addition of 200 μmol/L acetosyringone AS), for culturing at 28° C. and 180 r/min until $OD_{600}$=0.5-0.6.

A formula of the induction culture medium was: K-buffer 0.8 ml; M-N solution 1.8 ml; 1% $CaCl_2$) 0.08 ml; 0.01% FeSO4 0.8 ml; 20% NH4NO3 0.23 ml; Spore elements 0.48 ml; 50% glycerol 0.8 ml; 1 mol/L pH5.3 MES 3.8 ml and 2 mol/L dextrose 0.48 ml, which were diluted with sterile ddH2O to 100 ml.

The K-buffer consisted of K2HPO4 18 g and KH2PO4 14 g, which were adjusted to a pH value 6.8 with KOH, and diluted with sterile ddH2O to 100 ml.

The M-N solution consisted of MgSO4.7H2O 2.8 g and NaCl 1.3 g, which were diluted with sterile ddH2O to 100 ml.

The Spore elements consisted of 450 mg/L ZnSO4.7H2O, 450 mg/L CuSO4.5H2O, 450 mg/L H3BO3, 450 mg/L MnSO4.H2O and 450 mg/L NaMoO4.2H2O which were mixed at equal volume proportions, filtered and sterilized, and stored at 4° C.

4. *Agrobacterium* Infecting a Foxtail Millet Grain-Shiitake Mycelium Matrix (1) About 1 g of the cultured foxtail millet grains were added into a glass test tube, added with 1.3 ml of the induction culture medium (without addition of acetosyringone AS), subjected to ultrasonic treatment (under a frequency of 60 KHz and a power of 150 W) with a dual-frequency ultrasonic cleaner of Shanghai Kudos Ultrasonic instrument co., Ltd. for 1.5 min, and then was placed for 10 min. The supernatant was removed by absorption.

(2) 1.3 ml of the *agrobacterium* bacterial liquid well shaken in Step 3 was added, subjected to ultrasonic treatment with the dual-frequency ultrasonic cleaner of Shanghai Kudos Ultrasonic instrument co., Ltd. for 20 s (under a frequency of 50 KHz, a power of 150 W), and subjected to static infection for 25 min. The redundant bacterial liquid was removed by absorption, and static culturing was performed at 20° C. for 72 hours or more, wherein shaking was performed twice every day during the culturing.

(3) The foxtail millet grain individuals were transferred to induction culture medium plates (containing 5 mg/L hygromycin Hyg, 400 mg/L cefotaxime sodium cef, and 200 μmol/L AS), for culturing at 20° C. for 10 days, with 25 grains being inoculated on each plate.

Example 9

A method for genetic transformation of shiitake provided in the present example included following steps:

1. Preparation of a Foxtail-Millet-Grain Culture Medium (1) Foxtail millets were cleaned, soaked with distilled water for 22 minutes until the foxtail millets become slightly soft, and dispersed on a clean gauze for absorbing moisture.

(2) 30 g of the foxtail millets were weighed, placed into a triangular flask of 250 ml, and subjected to high-temperature high-pressure sterilization (120° C., 32 min).

2. Inoculation of Shiitake Mycelia (1) Shiitake mycelia cultured on a potato-dextrose-agar (PDA) culture medium for 7 days, together with the culture medium (55 mm×55 mm), were transferred into a homogenizer, added with 100 ml of a potato-dextrose-broth (PDB) culture medium, and they were intermittently smashed for 35 s.

(2) 10 ml of the above liquid mycelia were inoculated into the foxtail-millet-grain culture medium for culturing at 22.5° C. for 9 days, wherein shaking was performed every day during the culturing until the foxtail millet grains became white.

3. Activated Culturing of *Agrobacterium*

(1) *Agrobacterium* containing a binary expression vector GpiE was subjected to streak inoculation on LB solid culture medium containing corresponding antibiotics (20 mg/L rifampicin rif, 50 mg/L kanamycin Kan), for culturing at 28° C. for 3 days. The formula of 1 L of the LB solid culture medium contained: tryptone 10 g, yeast extract 5 g, sodium chloride 10 g and agar 15 g.

(2) Single colonies were picked and inoculated into 5 mL of an LB liquid culture medium (containing 20 mg/L rifampicin rif, 50 mg/L kanamycin Kan) for culturing at 28° C. and 220 r/min until OD600=0.5-0.6. The formula of 1 L of the LB liquid culture medium contained: tryptone 10 g, yeast extract 5 g and sodium chloride 10 g.

(3) 200 μl of the above *agrobacterium* bacterial liquid was re-suspended in 5 mL of the induction culture medium (with addition of 200 μmol/L acetosyringone AS), for culturing at 28° C. and 220 r/min until OD600=0.5-0.6.

A formula of the induction culture medium comprises: K-buffer 1.2 ml; M-N solution 2.2 ml; 1% $CaCl_2$) 0.12 ml; 0.01% FeSO4 1.2 ml; 20% NH4NO3 0.27 ml; Spore elements 0.52 ml; 50% glycerol 1.2 ml; 1 mol/L pH5.3 MES 4.2 ml; 2 mol/L dextrose 0.52 ml, which were diluted with sterile ddH2O to 100 ml.

The K-buffer consisted of K2HPO4 22 g and KH2PO4 15 g, which were adjusted to a pH value 7.2 with KOH, and diluted with sterile ddH2O to 100 ml.

The M-N solution consisted of $MgSO_4.7H_2O$ 3.2 g and NaCl 1.7 g, which were diluted with sterile $ddH_2O$ to 100 ml.

The Spore elements consisted of 550 mg/L $ZnSO_4.7H_2O$, 550 mg/L $CuSO_4.5H_2O$, 550 mg/L $H_3BO_3$, 550 mg/L $MnSO_4.H_2O$ and 500 mg/L $NaMoO_4.2H_2O$ which were mixed at equal volume proportions, filtered and sterilized, and stored at 4° C.

4. *Agrobacterium* Infecting a Foxtail Millet Grain-Shiitake Mycelium Matrix (1) About 1 g of the cultured foxtail millet grains were added into a glass test tube, added with 1.7 ml of the induction culture medium (without addition of acetosyringone AS), subjected to ultrasonic treatment (under a frequency of 50 KHz and a power of 140 W) with a dual-frequency ultrasonic cleaner of Shanghai Kudos Ultrasonic instrument co., Ltd. for 2 min, and then was placed for 10 min. The supernatant was removed by absorption.

(2) 1.7 ml of the *agrobacterium* bacterial liquid well shaken in Step 3 was added, subjected to ultrasonic treatment with the dual-frequency ultrasonic cleaner of Shanghai Kudos Ultrasonic instrument co., Ltd. for 15 s (under a frequency of 60 KHz, a power of 140 W), and subjected to static infection for 30 min. The redundant bacterial liquid was removed by absorption, and static culturing was performed at 22.5° C. for 72 hours or more, wherein shaking was performed twice every day during the culturing.

(3) The foxtail millet grain individuals were transferred to induction culture medium plates (containing 5 mg/L hygromycin Hyg, 400 mg/L cefotaxime sodium cef, and 200 μmol/L AS), for culturing at 22.5° C. for 8.5 days, with 25 grains being inoculated on each plate.

To sum up, the method for genetic transformation of edible mushrooms provided in the present disclosure uses the foxtail millet grains as attachment carrier for growth of the *Agaricus bisporus* mycelia or the enoki mushroom mycelia or the shiitake mycelia, and during the pre-culturing and co-culturing, the culture substrate is shaken up every day, so that the mycelia grow evenly on the foxtail millet grains, moreover, with impact force generated during shaking, wounds can be randomly created on the mycelia attached to the foxtail millet grains, which is more advantageous for performing the infection reaction with the *agrobacterium*, and significantly improves the transformation rate. Moreover, through the ultrasonic treatment, it can significantly promote the *agrobacterium* to infect the mycelia and improve the transformation rate; moreover, each foxtail millet grain can be used as a separate transformation individual, then the operation and statistics are more quick and convenient, and the separation is also easier. To sum up, compared with the existing genetic transformation methods, the method for genetic transformation of edible mushrooms provided in the present disclosure is convenient in operation, high in transformation efficiency, easy in transformant separation, and has a good application prospect.

The above are merely preferred examples of the present disclosure and not used to limit the present disclosure. For one skilled in the art, various modifications and changes may be made to the present disclosure. Any modifications, equivalent substitutions, improvements and so on, without departing from the spirit and principle of the present disclosure, should be covered by the scope of protection of the present disclosure.

INDUSTRIAL APPLICABILITY

The method for genetic transformation of edible mushrooms provided in the present disclosure uses the foxtail millet grains as attachment matrix for growth of the *Agaricus bisporus* mycelia or the enoki mushroom mycelia or the shiitake mycelia, and during the pre-culturing and co-culturing, the culture substrate is shaken up every day, so that the mycelia grow evenly on the foxtail millet grains, moreover, with impact force generated during shaking, wounds can be randomly created on the mycelia attached to the foxtail millet grains, which is more advantageous to the *agrobacterium* infection reaction, and improves the transformation rate. Through the ultrasonic treatment, it can significantly promote the *agrobacterium* to infect the mycelia and improve the transformation ratio; moreover, each foxtail millet grain can be used as a separate transformation individual, then the operation and statistics are more quick and convenient, and the separation is also easier. Compared with the existing genetic transformation methods, the method for genetic transformation of edible mushrooms provided in the present disclosure is convenient in operation, high in transformation efficiency, easy in transformant separation, and has a good application prospect.

What is claimed is:

1. A method for genetic transformation of *Agaricus bisporus*, said method comprising:
   step (a): inoculating *Agaricus bisporus* liquid mycelia into a foxtail millet grain culture medium, and placing them in a condition of 20-25° C. for pre-culturing until *Agaricus bisporus* mycelia grow on surfaces of foxtail millet grains, wherein the foxtail millet grain culture medium is shaken up every day during the pre-culturing;
   step (b): mixing the foxtail millet grains having the *Agaricus bisporus* mycelia with an induction culture medium, performing ultrasonic treatment and soaking treatment, discarding the culture medium supernatant, and collecting precipitated foxtail millet grains;
   step (c): mixing the foxtail millet grains obtained in step (b) with an *Agrobacterium* infection liquid containing target genes, performing ultrasonic treatment and static infection, absorbing redundant *Agrobacterium* bacterial liquid for removal, and performing co-culturing in a condition of 20-25° C., wherein the foxtail millet grains are shaken up every day during the co-culturing; and
   step (d): picking, after the co-culturing has ended, individual foxtail millet grains and transferring them to a screening culture medium, and performing screening culturing in a condition of 20-25° C.

2. The method for genetic transformation of *Agaricus bisporus* of claim 1, wherein 100 ml of the induction culture medium contains: K-buffer 0.8-1.2 ml, M-N solution 1.8-2.2 ml, 1% $CaCl_2$ 0.08-0.12 ml, 0.01% $FeSO_4$ 0.8-1.2 ml, 20% $NH_4NO_3$ 0.23-0.27 ml, spore elements 0.48-0.52 ml, 50% glycerol 0.8-1.2 ml, 1 mol/L pH5.3 MES (2-(4-morpholino)ethanesulfonic acid) 3.8-4.2 ml and 2 mol/L dextrose 0.48-0.52 ml, wherein the K-buffer contains per 100 ml: $K_2HPO_4$ 18-22 g and $KH_2PO_4$ 14-15 g; and a pH value of the K-buffer is 6.8-7.2, the M-N solution contains per 100 ml: $MgSO_4 \cdot 7H_2O$ 2.8-3.2 g and NaCl 1.3-1.7 g, and the spore elements are obtained by mixing 450-550 mg/L $ZnSO_4 \cdot 7H_2O$, 450-550 mg/L $CuSO_4 \cdot 5H_2O$, 450-550 mg/L $H_3BO_3$, 450-550 mg/L $MnSO_4 \cdot H_2O$ and 450-550 mg/L $NaMoO_4 \cdot 2H_2O$ with equal volume proportions.

3. The method for genetic transformation of *Agaricus bisporus* of claim 2, wherein 100 ml of the induction culture medium contains: the K-buffer 1 ml, M-N solution 2 ml, 1% $CaCl_2$) 0.01 ml, 0.01% $FeSO_4$ 1 ml, 20% $NH_4NO_3$ 0.25 ml, spore elements 0.5 ml, 50% glycerol 1 ml, the 1 mol/L pH5.3 MES 4 ml and the 2 mol/L dextrose 0.5 ml.

4. The method for genetic transformation of *Agaricus bisporus* of claim 2, wherein 100 ml of the K-buffer contains: $K_2HPO_4$ 20 g and $KH_2PO_4$ 14.5 g; and a pH value of the K-buffer is 7.0.

5. The method for genetic transformation of *Agaricus bisporus* of claim 2, wherein 100 ml of the M-N solution contains: $MgSO_4 \cdot 7H_2O$ 3 g and NaCl 1.5 g.

6. The method for genetic transformation of *Agaricus bisporus* of claim 1, wherein in step (b), a mass volume ratio (g:ml) of the foxtail millet grains to the induction culture medium is 1:1.3-1.7; and a volume of the *Agrobacterium* infection liquid used in step (c) is consistent with a volume of the induction culture medium used in step (b).

7. The method for genetic transformation of *Agaricus bisporus* of claim 1, wherein in step (b), the ultrasonic treatment is carried out under a frequency of 40-60 KHz and a power of 140-160 W for 1 min-2 min; and the soaking treatment lasts for 10-15 min.

8. The method for genetic transformation of *Agaricus bisporus* of claim 1, wherein in step (b), the ultrasonic treatment is carried out under a frequency of 40-60 KHz and a power of 140-160 W for 10 s-30 s; and the static infection lasts for 20-30 min.

9. The method for genetic transformation of *Agaricus bisporus* of claim 1, wherein 1 L of the screening culture medium contains: potato 190-210 g, dextrose 18-22 g and agar powder 18-22 g.

10. The method for genetic transformation of *Agaricus bisporus* of claim 1, wherein the foxtail millet grain culture medium in step (a) is prepared through a following method: cleaning the foxtail millet grains, soaking the foxtail millet grains with distilled water for 18-30 min to make the foxtail millet grains become slightly soft, dispersing the foxtail millet grains on a gauze for absorbing moisture, then placing the foxtail millet grains into a triangular flask, and carrying out high-temperature high-pressure sterilization to obtain the foxtail millet grain culture medium.

11. A method for genetic transformation of Enoki mushroom, said method comprising:
   (a) transferring enoki mushroom mycelia cultured on a solid culture medium, together with the culture medium, into a homogenizer, adding a liquid culture medium, intermittently smashing the same to obtain liquid mycelia, and inoculating the liquid mycelia into a foxtail millet grain culture medium for culturing at 20-25° C. for 8-10 days, wherein shaking is performed every day during the culturing until the foxtail millet grains become white;
   (b) carrying out streak inoculation for *Agrobacterium* containing a binary expression vector on a solid culture medium containing corresponding antibiotics, culturing the *Agrobacterium* at 28° C. for 2-3 days, then picking and inoculating single colonies in the liquid culture medium for culturing at 28° C. and 180-220 r/min until $OD_{600}$=0.5-0.6, and then re-suspending an *Agrobacterium* bacterial liquid in an induction culture medium for culturing at 28° C. and 180-220 r/min until $OD_{600}$=0.5-0.6;
   (c) adding the foxtail millet grains in step (a) to a container, adding the induction culture medium, performing ultrasonic treatment and soaking treatment, and removing a supernatant by absorption, wherein the ultrasonic treatment is carried out under a frequency of 40-60 KHz and a power of 140-160 W for 1 min-2 min, and the soaking treatment lasts for 10-15 min; and
   (d) adding to step (c) the *Agrobacterium* bacterial liquid of step (b), performing ultrasonic treatment and static infection, absorbing redundant bacterial liquid for removal, and performing culturing in a condition of 20-25° C. for 72 hours or more, wherein shaking is performed every day during the culturing; and finally, picking and transferring individual foxtail millet grains to induction culture medium plates for culturing at 20-25° C. for 7-10 days, wherein the ultrasonic treatment is carried out under a frequency of 40-60 KHz and a power of 140-160 W for 10 s-20 s, and the static infection lasts for 20-30 min.

12. The method for genetic transformation of enoki mushroom of claim 11, wherein the induction culture medium in step (b) and step (c) is prepared by mixing K-buffer 1 ml, M-N solution 2 ml, 1% $CaCl_2$ 0.1 ml, 0.01% $FeSO_4$ 1 ml, 20% $NH_4NO_3$ 0.25 ml, spore elements 0.5 ml, 50% glycerol 1 ml, 1 mol/L pH5.3 MES 4 ml and 2 mol/L dextrose 0.5 ml, and then diluting them with sterile $ddH_2O$ to 100 ml, wherein the K-buffer contains per 100 ml: $K_2HPO_4$ 18-22 g and KH$_2$PO$_4$ 14-15 g; and a pH value of the K-buffer is 6.8-7.2, the M-N solution contains per 100 ml: MgSO$_4$.7H$_2$O 2.8-3.2 g and NaCl 1.3-1.7 g, and the spore elements are obtained by mixing 450-550 mg/L ZnSO$_4$.7H$_2$O, 450-550 mg/L CuSO$_4$.5H$_2$O, 450-550 mg/L H$_3$BO$_3$, 450-550 mg/L MnSO$_4$.H$_2$O and 450-550 mg/L NaMoO$_4$.2H$_2$O with equal volume proportions.

13. A method for genetic transformation of Shiitake mushroom, said method comprising:
 (a) transferring shiitake mycelia cultured on a solid culture medium, together with the culture medium, into a homogenizer, adding a liquid culture medium, intermittently smashing the same to obtain liquid mycelia, and then inoculating the liquid mycelia into a foxtail millet grain culture medium for culturing at 20-25° C. for 15-20 days, wherein shaking is performed every day during the culturing until foxtail millet grains become white;
 (b) carrying out streak inoculation for *Agrobacterium* containing a binary expression vector on a solid culture medium containing corresponding antibiotics, culturing the *Agrobacterium* at 28° C. for 2-3 days, then picking and inoculating single colonies in the liquid culture medium for culturing at 28° C. and 180-220 r/min until OD$_{600}$=0.5-0.6, and then re-suspending the *Agrobacterium* bacterial liquid in an induction culture medium for culturing at 28° C. and 180-220 r/min until OD$_{600}$=0.5-0.6;
 (c) adding the foxtail millet grains in step (a) to a container, adding the induction culture medium, performing ultrasonic treatment and soaking treatment, and removing a supernatant by absorption, wherein the ultrasonic treatment is carried out under a frequency of 40-60 KHz and a power of 140-160 W for 1 min-2 min; the soaking treatment lasts for 10-15 min;
 (d) adding the *Agrobacterium* bacterial liquid of step (b) to step (c), performing ultrasonic treatment and static infection, absorbing redundant bacterial liquid for removal, and performing culturing in a condition of 20-25° C. for 72 hours or more, wherein shaking is performed every day during the culturing; finally; and picking and transferring individual foxtail millet grains to induction culture medium plates for culturing at 20-25° C. for 7-10 days, wherein the ultrasonic treatment is carried out under a frequency of 40-60 KHz and a power of 140-160 W for 10 s-20 s; the static infection lasts for 20-30 min.

14. The method for genetic transformation of Shiitake mushroom of claim 13, wherein the foxtail millet grain culture medium in step (a) is prepared by cleaning the foxtail millet grains, soaking the foxtail millet grains with distilled water for 18-30 min to make the foxtail millet grains become slightly soft, dispersing the foxtail millet grains on a gauze for absorbing moisture, then placing the foxtail millet grains into a triangular flask, and carrying out high-temperature high-pressure sterilization.

15. The method for genetic transformation of Shiitake mushroom of claim 13, wherein the induction culture medium in step (b) and step (c) is prepared by mixing K-buffer 1 ml, M-N solution 2 ml, 1% CaCl$_2$) 0.1 ml, 0.01% FeSO$_4$ 1 ml, 20% NH$_4$NO$_3$ 0.25 ml, spore elements 0.5 ml, 50% glycerol 1 ml, 1 mol/L pH5.3 MES 4 ml and 2 mol/L dextrose 0.5 ml, and then diluting them with sterile ddH$_2$O to 100 ml, wherein the K-buffer contains per 100 ml: K$_2$HPO$_4$ 18-22 g and KH$_2$PO$_4$ 14-15 g; and a pH value of the K-buffer is 6.8-7.2, the M-N solution contains per 100 ml: MgSO$_4$.7H$_2$O 2.8-3.2 g and NaCl 1.3-1.7 g, and the spore elements are obtained by mixing 450-550 mg/L ZnSO$_4$.7H$_2$O, 450-550 mg/L CuSO$_4$.5H$_2$O, 450-550 mg/L H$_3$BO$_3$, 450-550 mg/L MnSO$_4$.H$_2$O and 450-550 mg/L NaMoO$_4$.2H$_2$O with equal volume proportions.

16. The method genetic transformation of Shiitake mushroom of claim 15, wherein the K-buffer in the induction culture medium is prepared by mixing K$_2$HPO$_4$ 20 g and KH$_2$PO$_4$ 14.5 g, adjusting a pH value to 7.0 with KOH, and diluting them with sterile ddH$_2$O to 100 ml; and/or
 the M-N solution is prepared by mixing MgSO$_4$.7H$_2$O 3 g and NaCl 1.5 g, then diluting them with sterile ddH$_2$O to 100 ml; and/or
 the spore elements is prepared by mixing 450-550 mg/L ZnSO$_4$.7H$_2$O, 450-550 mg/L CuSO$_4$.5H$_2$O, 450-550 mg/L H$_3$BO$_3$, 450-550 mg/L MnSO$_4$.H$_2$O and 450-550 mg/L NaMoO$_4$.2H$_2$O with equal volume proportions, performing filtering and sterilizing, and storing them at 4° C.

17. The method for genetic transformation of Shiitake mushroom of claim 13, wherein the ratio of the foxtail millet grains to the induction culture medium to the *Agrobacterium* bacterial liquid added in step (c) is 1 g:(1.3-1.7) ml:(1.3-1.7) ml.

\* \* \* \* \*